(12) United States Patent
Stumpel

(10) Patent No.: US 9,519,749 B2
(45) Date of Patent: Dec. 13, 2016

(54) SURGICAL GUIDE AND METHOD

(71) Applicant: Lambert J. Stumpel, San Francisco, CA (US)

(72) Inventor: Lambert J. Stumpel, San Francisco, CA (US)

( * ) Notice: Subject to any disclaimer, the term of this patent is extended or adjusted under 35 U.S.C. 154(b) by 352 days.

(21) Appl. No.: 14/270,138

(22) Filed: May 5, 2014

(65) Prior Publication Data

US 2014/0244016 A1    Aug. 28, 2014

Related U.S. Application Data

(63) Continuation of application No. 12/975,104, filed on Dec. 21, 2010, now Pat. No. 8,714,975.

(60) Provisional application No. 61/289,310, filed on Dec. 22, 2009, provisional application No. 61/349,779, filed on May 28, 2010.

(51) Int. Cl.
    *A61C 8/00* (2006.01)
    *G06F 17/50* (2006.01)
    *A61C 1/08* (2006.01)

(52) U.S. Cl.
    CPC ........... *G06F 17/5086* (2013.01); *A61C 1/084* (2013.01); *A61C 8/009* (2013.01); *A61C 8/0089* (2013.01)

(58) Field of Classification Search
    CPC ....... A61C 1/084; A61C 8/0089; A61C 8/009; A61C 9/004; A61C 13/0004
    See application file for complete search history.

(56) References Cited

U.S. PATENT DOCUMENTS

| | | |
|---|---|---|
| 1,407,840 A | 2/1922 | Cruttenden |
| 2,634,501 A | 4/1953 | Linet |
| 5,015,183 A | 5/1991 | Fenick |
| 5,320,529 A | 6/1994 | Pompa |
| 5,556,278 A | 9/1996 | Meitner |
| 5,575,656 A | 11/1996 | Hajjar |

(Continued)

FOREIGN PATENT DOCUMENTS

| | | |
|---|---|---|
| CA | 2484475 | 4/2006 |
| CA | 2505283 | 10/2006 |

OTHER PUBLICATIONS

"CADImplant—Implanting with Ease™", CADImplant, Inc, Champfeuillet, France (2004).

(Continued)

*Primary Examiner* — Ralph Lewis
(74) *Attorney, Agent, or Firm* — Santa Fe IP, LLC

(57) ABSTRACT

A method for preparing a surgical guide for positioning of a dental implementation. The method includes positioning a positioning device relative to a model jawbone, translating the positioning device in a BL direction, adjusting a BL angle of the positioning device about a BL pivot axis corresponding to a desired position of a top of the dental implementation, and fixing the BL position, BL angle, and z-height of the positioning device. A mounting assembly mounts to the positioning device and includes a removable rotation block with a guide hole. The mounting assembly is movable in the MD direction while the BL position is fixed. A template fixes the mounting assembly for transferring the positioning information to a patient's mouth. Various aspects of the design process can be performed on a computer. The guide and a method of using the guide to perform an implant procedure are also disclosed.

13 Claims, 20 Drawing Sheets

(56) References Cited

U.S. PATENT DOCUMENTS

| | | | |
|---|---|---|---|
| 5,800,168 | A | 9/1998 | Cascione et al. |
| 5,833,693 | A | 11/1998 | Abrahami |
| 6,537,067 | B1 | 3/2003 | Wennemann |
| 6,634,883 | B2 | 10/2003 | Ranalli |
| 6,644,969 | B2 | 11/2003 | Kumar |
| 6,814,575 | B2* | 11/2004 | Poirier .................. A61C 1/084 433/75 |
| 6,869,283 | B2 | 3/2005 | Sussman |
| 6,913,463 | B2 | 7/2005 | Blacklock |
| 6,966,772 | B2* | 11/2005 | Malin .................... A61C 1/084 433/215 |
| 6,971,877 | B2 | 12/2005 | Harter |
| 7,014,461 | B2 | 3/2006 | Weinstein |
| 7,044,735 | B2 | 5/2006 | Malin |
| 7,086,860 | B2 | 8/2006 | Schuman et al. |
| 7,097,451 | B2 | 8/2006 | Tang |
| 7,574,025 | B2* | 8/2009 | Feldman ................. A61C 1/084 382/128 |
| 7,905,726 | B2 | 3/2011 | Stumpel |
| 8,521,317 | B2 | 8/2013 | Schneider et al. |
| 8,714,975 | B2* | 5/2014 | Stumpel ................. A61C 1/084 433/75 |
| 2004/0219479 | A1 | 11/2004 | Malin et al. |
| 2005/0142517 | A1 | 6/2005 | Frysh et al. |
| 2006/0257817 | A1 | 11/2006 | Shelton |
| 2006/0281046 | A1 | 12/2006 | Heo |
| 2007/0059661 | A1 | 3/2007 | Dadi |
| 2007/0154862 | A1 | 7/2007 | Kim |
| 2008/0176187 | A1 | 7/2008 | Stumpel |
| 2009/0202959 | A1 | 8/2009 | Ajlouni et al. |
| 2009/0274990 | A1 | 11/2009 | Kim |
| 2011/0159455 | A1 | 6/2011 | Stumpel |

OTHER PUBLICATIONS

"iDent—ImplantMaster", http://www.ident-surgical.com/tec_01.htm (2007).

"Iit—Innovative Implant Techology", http://www.iiweb.com/product/description/IGS (2006).

"Masterialise Dental—Tooth Supported SurgiGuide", Materialise Group, Leuven, Belgium (2006).

"NOBELGUIDE™ Options", http://www.nobelbiocare.com/global/en/ClinicalProcedures/NobelGuide/options.htm (2008).

* cited by examiner

SURGICAL GUIDE AND METHOD

CROSS-REFERENCES TO RELATED APPLICATIONS

This application is a Continuation of U.S. patent application Ser. No. 12/975,104 filed Dec. 21, 2010, now U.S. Pat. No. 8,714,975, entitled SURGICAL GUIDE AND METHOD, which claims priority to U.S. Provisional Patent Application No. 61/289,310 filed Dec. 22, 2009, entitled SURGICAL GUIDE, and to U.S. Provisional Patent Application No. 61/349,779 filed May 28, 2010, entitled SURGICAL GUIDE AND METHOD, the entire contents of which applications is incorporated herein for all purposes by this reference.

BACKGROUND OF THE INVENTION

Field of the Invention

The present invention relates to a method of positioning a dental implant or surgical tool at a desired site. Various aspects of the present invention relate to a method of positioning a dental implant utilizing a dental model, preparing a surgical guide, using the surgical guide to perform an osteotomy and align a dental implant, and intra-oral placement of the dental implant. Various aspects of the present invention relate to a surgical guide for accurately determining a position for an implant and translating a position on a model to a site in a subject on which a procedure is to be performed.

Description of Related Art

Dental implants are an increasingly popular option for patients with missing teeth due to excessive decay, bone or gum damage, or accidents causing physical displacement and the like. Dental implants provide an attractive alternative to dentures because they look natural and require less maintenance. Implants further provide a stronger biting surface and allow patients to resume their normal diets.

In comparison to dentures, however, dental implant procedures involve costly and complex surgical work. More specifically, dental implant procedures generally involve the placement of a dental implant or abutment in the underlying jawbone as a foundation, and the subsequent attachment of a prosthetic to the implant above the gum line. Generally, a dental osteotomy must be performed to prepare the bone for placement of the implant. The implant is then inserted and fixed into the bone where it serves to hold the dental prosthetic. An important aspect of the implant plan is the accurate positioning of the implant in the bone.

The most difficult and skill-intensive part of the implant procedure is generally positioning of the drill to create the hole in the jawbone that will receive the implant. The hole must be formed at the precise desired location relative to adjacent teeth for a natural, attractive look and to reduce the risk of interference with the adjacent teeth. The hole must also be positioned in the proper location in the bone to ensure a solid base for the prosthetic. Inaccuracies in placing the hole can damage nearby vital structures such as nerves, blood vessels, sinus and neighboring teeth.

It is desirable to reduce the risk of mistakenly drilling in an incorrect position. Improper placement of the hole for the implant presents problems for the surgeon during placement of the implant in the bone. If the hole is not placed in the proper position in the jawbone, further drilling may be necessary. Even more troublesome, if bone has been mistakenly removed, new bone may have to be grafted or added to the site. Because the graft has to set and the tissue must heal, bone grafting generally requires an additional 3-6 months before a new attempt can be made. Positioning mistakes also require additional office visits by the patient, additional time to completion, and unnecessary discomfort. For these reasons, implant procedures typically require the expertise of specialized surgeons and usually are avoided by less experienced surgeons and general dentists.

Many tools and methods have been developed for increasing the accuracy, reliability, and ease with which a practitioner can perform the drilling operation. The most popular technique remains free-hand alignment. In the case of free-hand drilling, a surgeon draws upon his or her extensive experience to determine the proper trajectory and final location of the implant. Not only does this require a steady hand, but the surgeon must also make a judgment as to where the bone is located below the gum surface. Because the bone is masked under the gum tissue, and because it is difficult to fully inspect the site, the surgeon typically has great difficulty in determining the proper position in this initial step.

The flap method is the typical method for overcoming the problem of determining bone position below the gum line. The flap method involves physically cutting a flap of skin near the site and surveying the implant site to determine the position of the jawbone relative to the implant. This method increases the risk of infection and provides further discomfort for the patient.

Free-hand drilling also presents safety hazards and accuracy problems. Although the surgeon can initially determine where to drill, during the drilling procedure, the drill bit can "jump" or slip. The drill bit can also "walk" or move before the tip of the bit grabs or digs into the bone. Additionally, free-hand drilling requires the surgeon to act without a complete view of the mouth interior and implant site.

Model-based or lab-based methods allow improved positioning by allowing less invasive surveying of the implant site and advanced planning for the procedure. An exemplar of the prior art is U.S. Pat. No. 7,086,860 to Schuman et al. The Schuman method involves using tools to determine the size, angle, and position of the dental implant on a model cast. The cast is cut to determine the bone position. A graphic is then drawn on the model and tools are used to transfer the placement information of the graphic to the implant site. In the laboratory, the buccal-lingual ("BL") volume of bone is derived from the subtraction of the tissue depth as measured in the mouth through bone sounding. If the anatomy is followed, an accurate reflection of the available bone volume for the implant placement may be determined. The mesial-distal ("MD") positioning of the implant is derived from the transpositioning or translation of information from a radiograph onto the cast.

The above method has several limitations. The MD positioning in the lab is only an estimate and is not verifiable until transferred to the mouth. Also, this method usually only allows the surgeon to practice drilling on a model and does not assist with precisely transferring or mapping the determined drilling position from the model back to the implant site in the subject patient. Ultimately, the drilling procedure still requires a steady hand and drilling expertise. Another technique involves fashioning a drill guide from the model. Errors, however, still often occur when transferring the model positioning to the drill guide. Additionally, the drill guide does not allow for controlled adjustment.

U.S. Pat. No. 6,971,877 to Harter is directed to a dental tool formed of a stent and a bushing holder for guiding a drill bit. The stent is formed on a model and configured to fit a patient's jaw. The bushing holder fits into a hole in the stent.

A ball-and-socket joint allows a user to adjust the guide by pivoting a bushing within the bushing holder. Harter thus allows for transfer of information from the model to the patient's mouth. This adjustment, however, has the same limitations of free-hand adjustment because a user adjusts the guide in 3D space with little control.

Moreover, the Harter guide limits a user's ability to make adjustments to pivot angle independent of translational movement. The pivot point of the joint is positioned well above the occlusal plane and at a distance from the jawbone. Adjustments to the pivot angle above the teeth results in significant translation of the point of entry of the drill bit at the jawbone below. As the guide pivots, therefore, a correction must be made to the translation. This adds to the difficulty of achieving accurate positioning.

There is a continuing need to reduce the costs and complexities associated with existing implant procedures. Conventional techniques generally require many steps to be performed by different people. Such additional steps create undesirable consequent increases in overall cost and overall procedure time.

In light of the forgoing, it would be beneficial to have a method and apparatus for aligning a dental implant which overcomes the above and other disadvantages of known implant positioning systems and methods. What is needed is an improved method and apparatus for controllably and quantifiably determining and adjusting a desired guide trajectory that would allow accurately and repeatably performing a dental implant osteotomy and placing of a laboratory analog of an implant.

What is needed is a simple and easy-to-use dental guide device and method. What is needed is a method for planning and positioning a dental implant with increased flexibility. What is needed is a method that allows for various processes to be performed at different times and locations. What is a needed is a method for reducing the time to perform implant planning and positioning.

BRIEF SUMMARY OF THE INVENTION

The invention relates to a surgical guide for positioning a dental implementation such as a dental tool, implant, or prosthetic. One aspect of the present invention is directed to a method of preparing a surgical guide for buccal-lingual (BL) and mesial-distal (MD) positioning of a dental implementation. The method may include positioning a positioning device relative to a jawbone adjacent an edentulous area on a model of a patient's dental arch including translating the positioning device in a BL direction to a desired BL position axis that is in-line with the jawbone region, adjusting a BL angle of the positioning device about a BL pivot axis corresponding to a desired position of a top of the dental implementation to be positioned, the BL pivot axis being located on the BL position axis, and/or fixing the BL position and the BL angle of the positioning device relative to the model, and mounting a mounting assembly relative to the model, the mounting assembly including a mounting frame and an interim receiver block for receiving an upper portion of the positioning device such that the frame has a fixed BL position and BL angle relative to the positioning device, the mounting assembly being configured to receive the dental implementation.

The method may further include, before the positioning of the positioning device, indicating with reference points the jawbone region on the model, wherein the translating of the positioning device in the BL direction may be performed based on the reference points.

The positioning device may include a slot for visual alignment with a BL reference point.

The positioning of the positioning device about a BL pivot axis may include setting a z-height of the positioning device.

The mounting may include translating the mounting assembly in a MD direction to a desired MD position relative to the jawbone region, adjusting a preliminary MD angle of the mounting assembly about an MD pivot axis, the MD pivot axis being coextensive with the interim receiver block and the upper portion of the positioning device, and/or affixing the mounting frame to a template corresponding to the model.

The template may removably affix the mounting frame relative to the jawbone on the model.

The method may further include installing a rotation block relative to the model by removing the interim receiver block from the mounting frame, and/or removably mounting a rotation block to the mounting frame, wherein the rotation block may be selected from a set of rotation blocks, each including a guide hole therethrough having a predetermined MD position and MD angle.

The upper portion of the positioning device may define the MD pivot axis, the mounting frame being configured to rotate about the MD pivot axis while the BL position and BL angle are fixed.

The method may further include, after the installing, performing adjustment of the MD angle of the guide hole by replacing the rotation block with another rotation block having a different MD angle.

The method may further include transferring the template, mounting frame and rotation block from the model to the patient's dental arch, and securing the template and mounting frame to the patient's dental arch adjacent the edentulous area of the patient.

At least one of the rotation block and frame include may be configured to allow controllable translation of the rotation block relative to the frame.

The positioning device may include a slot for promoting buccal-lingual rotational alignment and translation in a z-direction of the positioning device relative to the jawbone.

The BL pivot axis may be located adjacent an upper portion of the jawbone.

The model may be a CAD model and the positioning of the positioning device may be performed on a computer.

Mounting of the mounting assembly may be accomplished by mounting the assembly to a physical model corresponding to the CAD model.

Replacing of the rotation block may be accomplished by replacing the rotation block when the template and mounting frame may be positioned in the edentulous area of the patient's dental arch.

A surgical guide assembly for positioning a dental implementation may be prepared according to the above methods.

Another aspect of the present invention is directed to a surgical guide assembly for a dental implant procedure, the guide assembly including a mounting assembly including a mounting frame and removable rotation block, the mounting frame configured to maintain a BL angle and BL position of the rotation block relative to at least one tooth adjacent an edentulous area based on a dental model, the rotation block including a guide for receiving a dental tool and having a predetermined MD position and MD angle, wherein the rotation block may be connected to the mounting frame at a BL pivot point defining the BL angle of the rotation block, the BL pivot point being adjacent a top portion of a jawbone and corresponding to a top of the implant to be implanted.

The predetermined MD angle may be one of about 0 degrees, about 3 degrees, and about 7 degrees.

The mounting frame may include rails for preliminary clamping to the at least one tooth.

The guide assembly may further include an interim receiver block interchangeable with the rotation block, the interim receiver block configured to receive a positioning device for positioning the mounting frame in a BL position and BL angle relative to the model.

The upper portion of the positioning device may be received in the receiver block, further wherein positioning device may be elongated and extends in an apical direction from the receiver block to a position adjacent a jawbone in-line with a desired trajectory of the dental tool.

The upper portion of the positioning device may include a pivot pin for rotationally fixing the positioning device to the model at the BL pivot point.

The rotation block may include a slot defining a MD pivot axis of the rotation block relative to the positioning device, the rotation block being configured to rotate about the MD pivot axis while the BL position and BL angle are fixed.

The positioning device may include a slot shaped to promote rotational alignment of positioning device with a BL reference point on the model.

A method of performing a dental implant procedure may include mounting a guide assembly on a dental arch, the guide assembly bridging the edentulous area, inserting a drill bit through the guide of the rotation block, the guide configured to maintain a trajectory of the drill bit into the jawbone, preparing the jawbone with a hole for receiving the implant using the drill bit, removing the drill bit from the guide, and/or inserting the implant through the guide assembly and into the hole, wherein the top of the implant may be in-line with the top portion of the jawbone.

Another aspect of the present invention is directed to a method of preparing a surgical guide for buccal-lingual (BL) and mesial-distal (MD) positioning of a dental implementation. The method may include mounting a mounting assembly relative to a jawbone adjacent an edentulous area on a model of a patient's dental arch, positioning the mounting assembly in a desired BL position that may be in-line with the jawbone region and at a desired BL angle, fixing the BL position and the BL angle of the mounting assembly relative to the model, removably attaching a guide insert to the mounting assembly, the BL position and BL angle of the guide insert fixed relative to the model by the mounting assembly, the mounting assembly and guide insert forming an interim surgical guide, and the guide having a bore configured to receive the dental implementation therethrough, and/or imaging the surgical guide on the patient's dental arch.

The mounting assembly may include a mounting frame for supporting the guide insert such that the BL position and BL angle of the frame and guide insert may be fixed relative to the model.

The positioning may be accomplished by translating the mounting assembly in the BL direction to the desired BL position, and separately adjusting the BL angle to the desired BL angle.

The above methods may further include, after the positioning of the BL position and BL angle translating the mounting assembly in a MD direction to a desired MD position relative to the jawbone region; and adjusting the mounting assembly about an MD pivot axis to a desired MD angle.

The mounting assembly may be configured to be translated and adjusted in the MD direction while the BL position and BL angle are fixed.

The guide insert may include a marker capable of being imaged with at least one of a CT scan or X-ray.

The above methods may further include, after the imaging, creating a computer-based model of the interim guide on the patient's dental arch based on information related to the resulting image.

The above methods may further include, determining a desired MD position and MD angle of the guide bore using the computer-based model.

The above methods may further include storing information related to the surgical guide in a memory.

The above methods may further include, fabricating a surgical guide based on the desired MD position and MD angle.

Yet another aspect of the present invention is directed to a computer program product for use in conjunction with a computer system. The program product may include a computer readable storage medium and a computer mechanism embedded therein, the mechanism including instructions for performing any one or more of the above methods.

The methods and guide assemblies of the present invention(s) have other features and advantages which will be apparent from or are set forth in more detail in the accompanying drawings, which are incorporated in and form a part of this specification, and the following Detailed Description of the Invention, which together serve to explain the principles of the present invention(s).

BRIEF DESCRIPTION OF THE DRAWINGS

FIG. 3(*b*) is a perspective view of the mounting assembly positioned on the positioning device of FIG. 1, the mounting assembly including an interim receiver block and frame. FIG. 3(*c*) is a perspective view of the mounting assembly of FIG. 3(*b*), illustrating removal of the interim receiver block and installation of a selected rotation block.

FIGS. 38, 39, 40, 41, 42, and 43 are sequential views illustrating a guide assembly similar to that of FIG. 28 being aligned with the model in accordance with the present invention.

FIG. 53 is illustrates alignment of the X-ray using the guide system in accordance with the present invention.

DETAILED DESCRIPTION OF THE INVENTION

Figure 1:
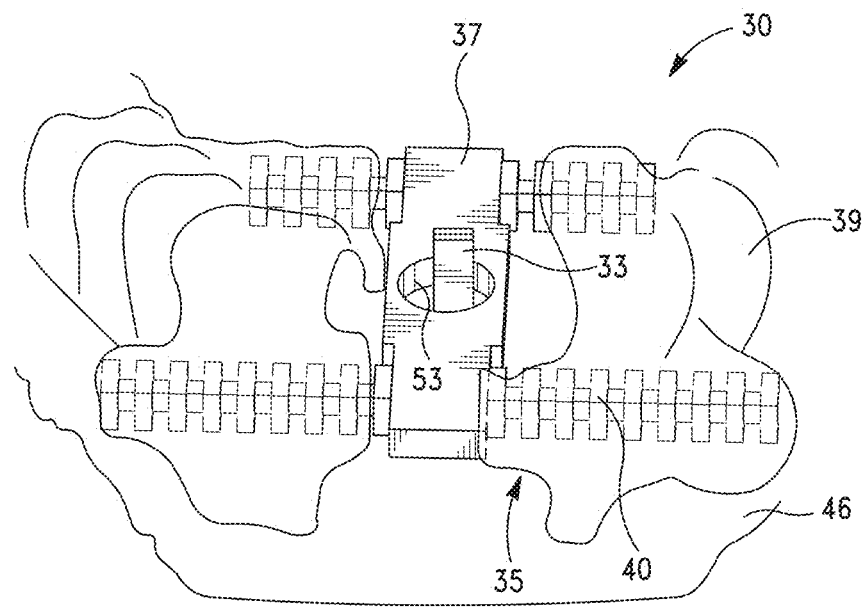
FIG. 1 is a front (posterior) view of a dental guide system positioned on a model in accordance with the present invention.

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

In many aspects, the present invention is similar to those described in U.S. patent application Ser. No. 11/870,310 filed Oct. 10, 2007, entitled SURGICAL GUIDE FOR DENTAL IMPLANTS AND METHOD THEREFOR, U.S. Provisional Patent Application No. 60/850,605 filed Oct. 10, 2006, entitled IMPLANT POSITIONING SYSTEM MODEL BASED, and U.S. Provisional Patent Application No. 61/289,310 filed Dec. 22, 2009, entitled SURGICAL GUIDE, the entire contents of which applications are incorporated herein for all purposes by this reference.

"Dental implementation" refers to devices and structures for use with the drill guide in accordance with the present invention. In various aspects, "dental implementation" refers to a drill bit, radiographic marker, or other tools for use in performing an osteotomy using the drill guide in accordance with the present invention. In various aspects, "dental implementation" refers to a dental prosthetic or implant to be placed at a desired location in a patient.

"Buccal", "lingual", "mesial", and "distal" are to be understood as generally used in the dental, orthodontic, and biomedical arts. In various aspects, "buccal-lingual" and "BL" generally refer to a direction in the buccal (cheek) and lingual (tongue) directions as determined at a respective location. In various aspects, "mesial-distal" and "MD" generally refer to a direction in the mesial (toward the front tooth) and distal (towards a rear tooth) directions as determined at a respective location.

"Osteotomy" is to be understood as generally used in the dental, orthodontic, and biomedical arts and generally refers to a procedure involving modification of bone at an implant site.

"Implant site" refers to a region of the edentulous area where an implant is to be placed.

"Edentulous" and/or "edentulous area" are to be understood as generally used in the dental, orthodontic, and biomedical arts and generally refer to a gap or space left by a missing tooth. In various aspects, "edentulous area" refers to a desired location where a dental prosthetic is to be placed and which is defined by a jawbone and/or tissue on the bottom and in-line with adjacent teeth. In various aspects, "edentulous area" refers to an area expected to be edentulous including, but not limited to, an area on a model where an edentulous is to be formed.

"Model" refers to both physical objects and virtual objects, such as a numerically-based software model.

"Prosthetic" is to be understood as generally used in the dental, orthodontic, and biomedical arts and includes both the singular and plural. "Prosthetic" generally refers to a device which is at least partially artificial and replaces a lost body part or assists with performing a body function. In various aspects, "prosthetic" is used interchangeably with "dental analog", "dental prosthetic", and "restoration". In various aspects, "prosthetic" refers to an artificial tooth for replacing a missing tooth in a patient's mouth.

"Implant" is to be understood as generally used in the dental, orthodontic, and biomedical arts and includes both the singular and plural. In various aspects "implant" is used interchangeably with "abutment" and "prosthetic implant abutment" and generally refers to an element or device used to anchor or support a prosthetic at a target site. In various aspects, "implant" refers to a device for connecting living bone and/or tissue to a prosthetic.

Figure 2:
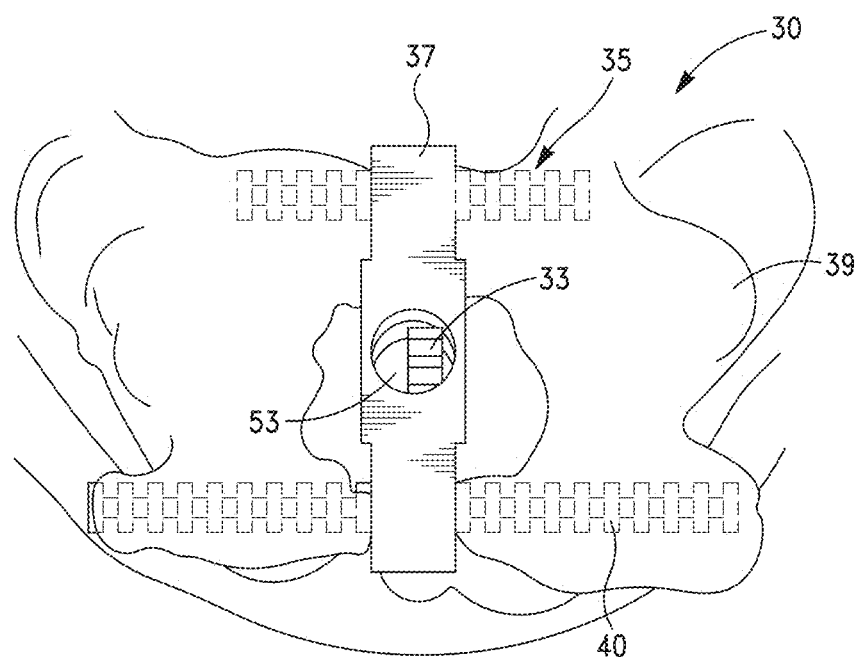
FIG. 2 is a top (occlusal) view of the guide system of FIG. 1.

Turning now to the drawings, wherein like components are designated by like reference numerals throughout the various figures, attention is directed to FIGS. 1-2 illustrating a surgical guide assembly, generally designated 30, positioned over an edentulous area 32 of a model based on a patient's mouth. The exemplary surgical guide assembly includes a positioning device 33, a mounting assembly 35, a removable rotation block 37, and a template 39. The template is configured to secure the guide assembly to the teeth on the model, and likewise, the teeth in the patient's mouth. Suitable materials for the template include, but are not limited to, orthodontic impression material, expandable foam, and polymers. The template may also be configured with a fastener or other device for attaching to the mounting assembly and teeth as would be appreciated by one of skill in the art from the foregoing.

As will be described in greater detail below, the surgical guide assembly generally allows for accurate transfer of a setup based on a jawbone and edentulous area on a model to a patient. The guide assembly in accordance with the present invention allows for isolating adjustment of the guide hole in a single or limited number of directions at a time thereby reducing the complexity of positioning the guide in three-dimensional (3D) space.

Mounting assembly 35 of the guide includes a mounting frame 40 and interim receiver block 54. As will be described in greater detail below, in the completed surgical guide the mounting frame supports the removable rotation block 37. The mounting frame fixes the rotation block relative to the template. In an intermediate step, the mounting assembly includes receiver block 54 and is configured to be adjusted in the MD plane relative to the model and thereafter fixed to the model using the template.

Positioning device 33 defines a position and angle of the mounting frame in the BL plane as will be described in greater detail below. The exemplary positioning device is an elongated post. A top portion 42 of the positioning device is dimensioned and configured to be received in interim receiver block 54 and subsequently guide hole 44 in rotation block 37.

In various embodiments, the guide hole of the rotation block is configured to receive and guide a dental drill and an implant. One will appreciate that the guide hole may be configured to receive and guide a variety of dental implementations. An optional sleeve may be provided for removable insertion into the guide hole to allow interchangeability with different devices. In an exemplary embodiment, an inner surface of the guide hole is metal to prevent the drill bit from destroying the rotation block. In various embodiments, the optional sleeve if formed of a rigid material to protect the rotation block. The inner diameter of the guide hole of the rotation block may also be dimensioned to correspond to the outer diameter of the drill bit such that a sleeve is not necessary. In various embodiments, the guide hole is manufactured to a minimum size and the diameter is increased incrementally until it fits the selected dental tool. In an exemplary embodiment, the rotation block has a height of about 4 mm and a guide hole diameter of about 5.5 mm. In an exemplary embodiment, the guide hole has a smaller diameter at the bottom than the top to allow for rotation in the hole. In an exemplary embodiment, the guide hole is round and slightly larger than the upper end of the positioning device to allow for an additional amount of adjustment after the rotation block is inserted.

Figure 9:
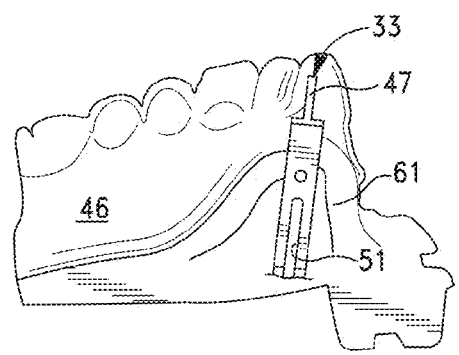
Figure 10:
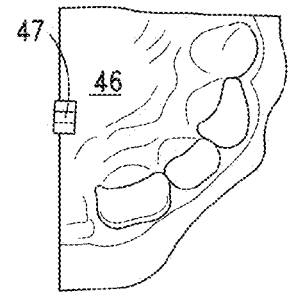

Referring generally to FIGS. 1-2, the surgical guide assembly is prepared based on a dental model 46 corresponding to a patient's mouth. The model is prepared by taking an impression of the patient's mouth and teeth or using other conventional techniques. A portion of positioning device 33 is attached to the model (see, e.g., FIG. 9), and a portion of mounting assembly 35 is fixed in position relative to the model based on the positioning device position (see, e.g., FIG. 20).

In accordance with the present invention, surgical guide assembly 30 is configured for guiding a drill bit during a dental osteotomy to prepare a jawbone for receiving an abutment. The exemplary guide assembly is also configured to guide the abutment to the prepared location along the actual jawbone. One will appreciate that the surgical guide assembly may be used for a variety of procedures and may be configured to guide a variety of tools and devices depending on the procedure to be performed.

Figure 3:
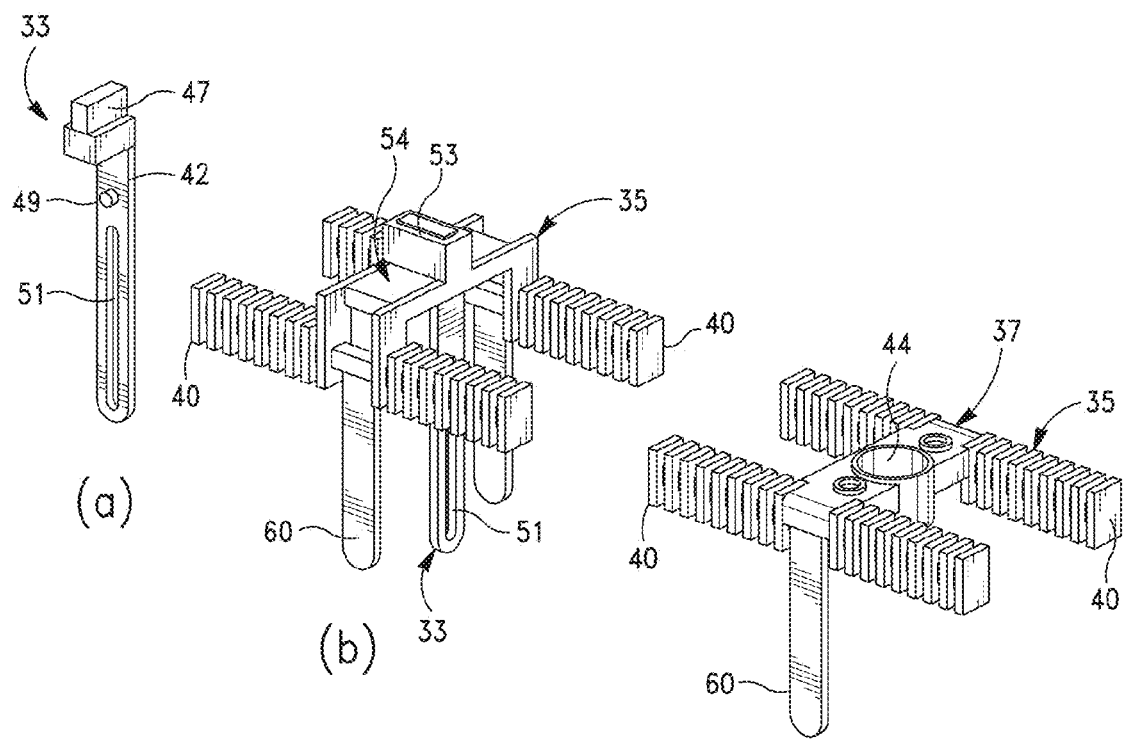
FIG. 3(*a*) is a perspective view of the positioning device of FIG. 1.
Figure 4:
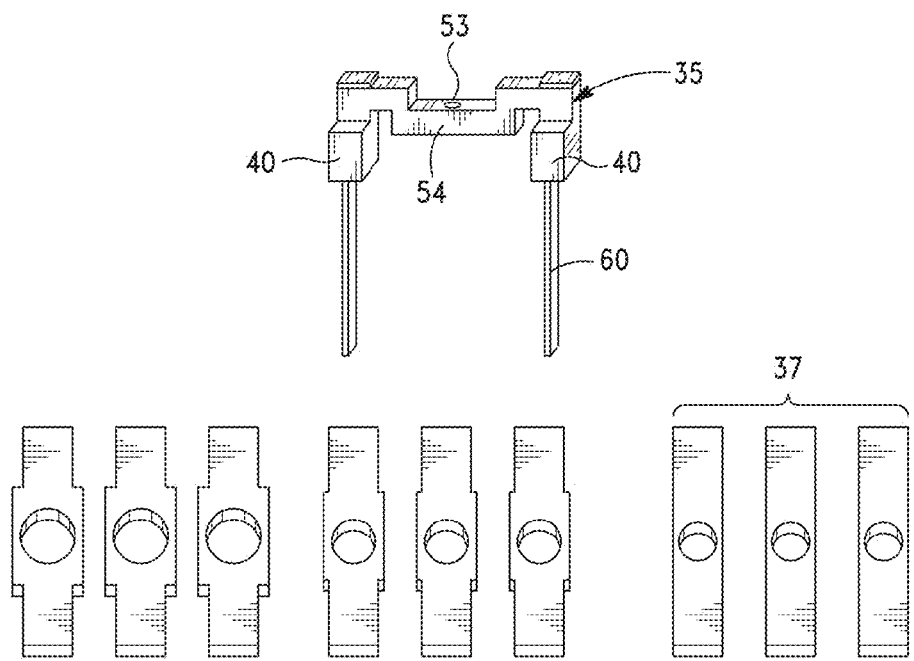
FIG. 4 is a perspective view of a kit for preparing the guide system of FIG. 1, illustrating a plurality of rotation blocks with different mesial-distal angles and different sizes of guide bores.
Figure 4:
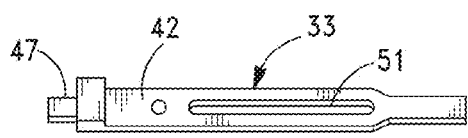

Referring to FIGS. 3(a), 3(b), 3(c), and 4, the surgical guide assembly in accordance with the present invention includes various components, some of which are designed for exclusive use during intermediate steps of making the guide assembly. The various components illustrated in FIG. 4 are intended to constitute a "kit" to be delivered to a surgeon or other dental practitioner for use.

As shown in FIG. 3(a), positioning device 33 is elongated with a tongue member 47 at upper portion 42. A pin 49 projects outward from a central portion of the positioning device. A portion of the positioning device includes a slot 51.

As shown in FIG. 3(b), positioning device 33 is configured to receive and position mounting assembly 35. Tongue 47 of positioning device 33 is configured to be inserted into and received within a receiving hole 53 of an interim receiver block 54. The exemplary receiver hole is dimensioned and configured to form a sufficiently tight fit with tongue 47 such that the receiving block and mounting frame are not free to move in the BL direction relative to the positioning device. In an exemplary embodiment, the receiving hole is dimensioned and configured to reduce or prevent BL rotation relative to the positioning device.

The exemplary mounting frame 40 includes rails 56 at each end of the interim receiving block 54. Each rail includes a longitudinal section 58 extending in the MD direction and a vertical section 60. The rails are configured to allow for clamping of the block to the teeth on the model. One will appreciate that other configurations may be employed for the mounting frame in order to mount the receiver block and/or rotation block to the teeth on the model. The mounting frame may be configured to mount to the teeth by mechanical (such as fasteners, adhesives, clamps, suction, and friction), ionic, chemical, other means as would be understood by one of ordinary skill in the art from the foregoing.

FIG. 3(c) illustrates mounting assembly 35 after the interim receiving block has been replaced with a selected rotation block 37. As shown in FIG. 4, the "kit" includes a number of rotation blocks and interim receiving blocks, each of which have guide holes and receiving holes, respectively, with predetermined angles. By "predetermined angle" it is meant that the hole has a fixed trajectory angle.

In an exemplary embodiment, the set of rotation blocks includes groups of rotations blocks having differing guide hole diameters, each group having MD angles of about 0 degrees, about 3 degrees, and about 7 degrees. The rotation block groups each have different-sized guide holes. In an exemplary embodiment, the guide hole diameters are about 4.1 mm, about 5.05 mm, and about 6.25 mm. In an exemplary embodiment, the guide hole sizes correspond to standard sizes provided by common implant manufacturers, such as Nobel Biocare of Zurich, Switzerland, Biomet 3i of Warsaw, Ind., and Straumann of Basel, Switzerland. One will appreciate that other suitable groupings may be provided.

Exemplary mounting frame 40, interim receiving block 54, and rotation block 37 are formed of nonreactive polymers. Exemplary positioning device 33 is formed of a nonreactive metal such as titanium, stainless steel, or gold. Suitable materials for these and other components of the guide assembly include, but are not limited to, metal, ceramic, and stereo-lithographic composite material. In various embodiments, the mounting frame is injected molded plastic. One will appreciate that the various components of the surgical guide may be optionally coated or treated for a predetermined biological response. For example, the components may be treated with a thrombogenic or platelet formation agent to promote faster healing. The components may also be treated to reduce undesirable biological responses and risk of infection. The receiving block and/or rotation block may be attached to the mounting frame using mechanical, ionic, chemical, or other means as would be understood by one of ordinary skill in the art from the foregoing.

The method of preparing the surgical guide assembly for buccal-lingual (BL) and mesial-distal (MD) positioning of a dental implementation in accordance with the present invention will now be described with general reference to FIGS. 5-28. Preparation of the guide assembly requires determining a location of a jawbone for receiving an implant. In various embodiments, the method includes creating a model by taking an impression of a patient's mouth. A physical model may be used for planning and subsequent assembly of the surgical guide. The exemplary model is fabricated from an ACCUTRAC® model base provided by Coltène/Whaledent Inc. of Cuyahoga Falls, Ohio. Alternatively, a cast model can be fabricated.

Figure 5:
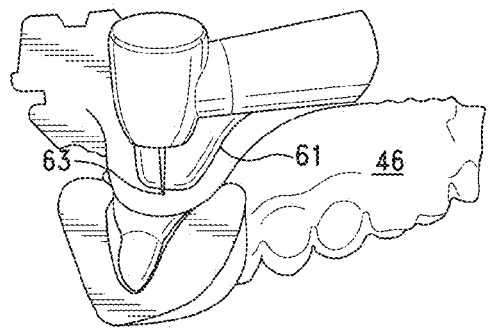
FIGS. 5, 6, 7, 8, 9, 10, 11 and 12 illustrate the positioning device of FIG. 1 being aligned with and fixed to a model in accordance with the present invention.
Figure 6:
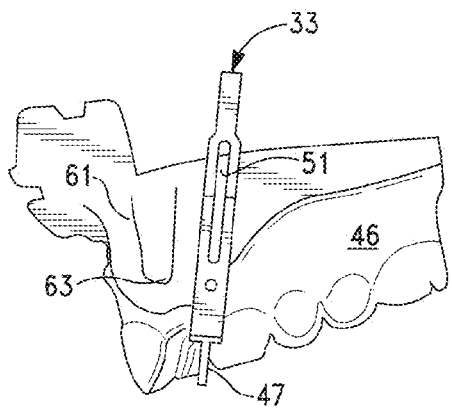

Conventional techniques such as sounding may be used to determine the general outline of the jawbone relative to the teeth. Once the model base is prepared, soft tissue depth measurements may be transferred to the cast model and the model is reduced accordingly. For example, the model may be cut along a BL plane through the edentulous area and an outline 61 may be provided on model 46 as shown in FIG. 5. Reference points are drawn on the model corresponding to the jawbone region and soft tissue depth. "Reference points" refers to lines, points, and other features. One will appreciate that other techniques may be used to demarcate the jawbone region on the model.

In various embodiments, the reference points influence the final location of the guide assembly in the BL plane. The practitioner uses the model to determine exactly where the implant should be positioned in the jawbone. A BL axis line is scribed on the model to denote where the implant should be positioned based on the jawbone and soft tissue location. As will described below, in various embodiments, the practitioner works off the references points to prepare the surgical guide. Since each step in the process builds off the reference points, the final surgical guide is not likely to require readjustment, which could introduce error. In various embodiments, the surgical guide is prepared without the use of reference points on the model. One will appreciate from the description herein that other techniques may be used to determine a desired location for the implant.

After the desired location of the implant is determined and the reference points are created on the model, a pivot hole 63 is drilled into the model based on the optional reference points, as shown in FIG. 5. The pivot hole is configured to mount the positioning device to the model. The pivot hole is made on or near the jawbone region and defines a BL pivot point. In various embodiments, the pivot hole corresponds to a location of the top of the implant which is to be implanted. The pivot hole thus represents a desired BL position for the implant. The exemplary pivot hole is positioned along a BL position axis extending through the modeled jawbone (best seen in FIG. 6). In various embodiments, the BL pivot point is adjacent a top portion of the jawbone and in-line with a lower portion of the crown of one or more adjacent teeth.

Figure 7:
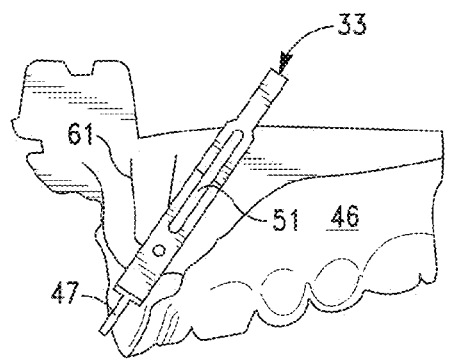

Pin 49 of positioning device 33 is inserted into pivot hole 63 to rotatably fasten the positioning device to the model, as shown in FIG. 7. The positioning device is moved in the BL direction until the pivot pin fits into the pivot hole. The pivot pin fixes the positioning device in the BL plane but allows for BL rotation. Thus, the BL position is fixed first and then the BL rotation may be adjusted. In an exemplary embodiment, the position of the positioning device on the model determines the resulting final BL position and BL angle of the implant. The exemplary positioning device lies flat against the cut surface of the model thereby providing preliminary positioning of MD angle.

With continued reference to FIG. 7, the position of pivot hole 63 determines the z-height of the positioning device, which in turn determines the height of the implant relative to the top of the ridge of the jawbone. It can thus be important to accurately position the exemplary pivot hole in the BL position and z-height on the model to avoid making adjustments in the patient's mouth later. In various embodiments, the height of the pivot hole is slightly above, in-line with, or slightly below the top ridge of the jawbone. Aside from the position of the outer contours of the jawbone, the BL pivot hole may also be determined based on a location of the nerves in the jawbone. The lower jawbone has a nerve canal protecting a large nerve. When implanting a device in the lower jawbone, therefore, it may be important to determine a position that does not interfere with the nerve canal.

Because the positioning is performed on a model, the hole can be moved as necessary until the desired position is found without affecting the patient. The model and reference points allow a user to determine with greater ease whether the positioning device is in a desired position. One will appreciate from the description herein that other methods and devices may be used to guide the positioning device to the desired BL position and z-height. For example, a slot or track may be provided for adjustable translation in the BL position, z-height, or both. The track may be configured with teeth or other features to provide course and fine adjustment.

After attaching positioning device 33 to the model, the BL angle of the positioning device is adjusted. The BL angle of the positioning device is adjusted by rotating the positioning device about the BL pivot axis defined by the pivot pin. Although the exemplary embodiment includes a pin-and-hole configuration, one will appreciate that other configurations may be used to allow for setting the BL position and subsequent BL rotation on the model.

One will appreciate that the model may be used in conjunction with indexing features and the like to aid in the positioning of the positioning device. For example, a guide tool may be used to enable the user to determine the angle of the positioning device relative to the z-axis. In various embodiments, the user creates indexing holes at measured rotational angles to aid in adjustment of the BL angle.

In various embodiments, the BL pivot axis corresponds to a desired position of a top of the dental implementation to be positioned. The positioning device is rotated such that it aligns with a BL reference line on the model. The BL reference line is determined by the user drawing on his or her expertise and represents a desired implant trajectory or BL axis in the jawbone. In various embodiments, the BL axis is determined based on the center of the jawbone region. In various embodiments, the BL axis is selected based on the thickest section (i.e. depth) of the jawbone. One will appreciate that the BL axis may also be based on the position of adjacent teeth and/or other factors.

Figure 8:
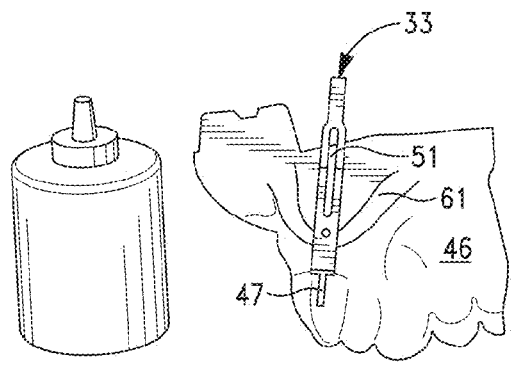

Exemplary positioning device 33 includes slot 51. In various embodiments, the slot promotes visual alignment of the positioning device with the BL reference line. As shown in FIGS. 7 and 8, the positioning device may be rotated until the BL reference line on the model is visible through the slot.

After the positioning device is in proper alignment with the jawbone on the model, the positioning device is optionally fixed into place such that the BL position and BL angle can not change. In other words, the positioning device is fixed in the two-dimensional (2D) plane defined by the cut plane of the model. The positioning device may be fixed into place using orthodontic glue and the like (shown in FIG. 9).

Figure 11:
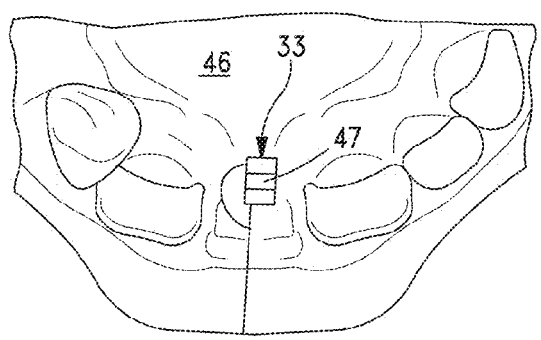
Figure 12:
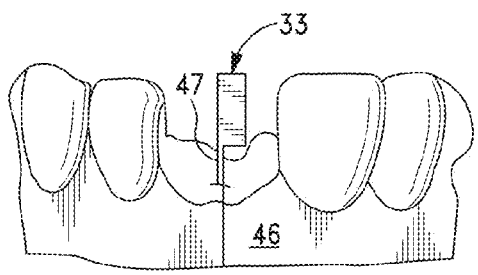

Referring to FIGS. 11 and 12, the model is reassembled with the positioned positioning device in place. With the model reassembled, a user can verify that the BL position and angle of the positioning device relative to the jawbone is proper. The process can be repeated if readjustments are necessary.

Figure 13:
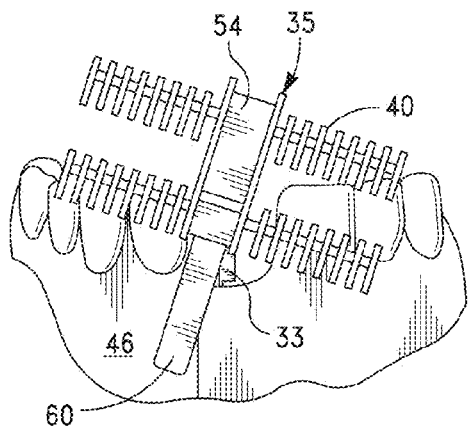
FIGS. 13 and 14 are sequential views illustrating the method of mounting of a mounting assembly to the fixed positioning device of FIG. 12.
Figure 14:
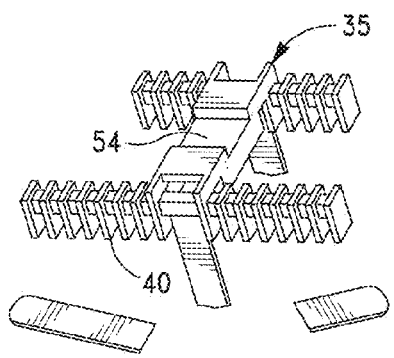
Figure 15:
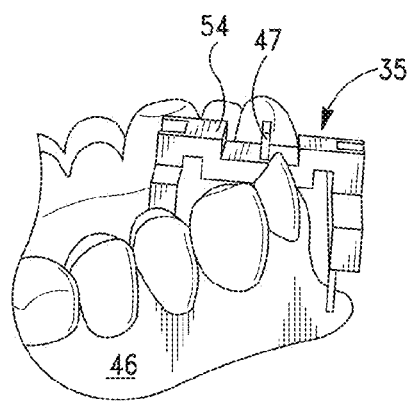
FIGS. 15, 16, 17, 18, 19 and 20 are sequential views illustrating the method of adjusting of the mounting assembly in the MD direction and adjusting the MD angle while holding the BL position and angle fixed.

Referring to FIGS. 13 and 14, mounting assembly 35 including interim receiver block 54 is next positioned over positioning device 33. Tongue 47 is inserted into receiving hole 53 of receiver block 54. The positioning device and receiver block are secured together such that the BL position of the receiver block is based on the BL position and BL angle of the positioning device. Mounting frame 40 is attached to the receiver block for temporary support. Rails 56 of the mounting frame may be trimmed and adjusted, if necessary, to accommodate the mounting frame on the teeth (see, e.g., FIG. 14). One will understand from the foregoing that the exemplary positioning device thus acts as an intermediate tool for determining a position of the surgical guide assembly in the BL plane.

Figure 16:
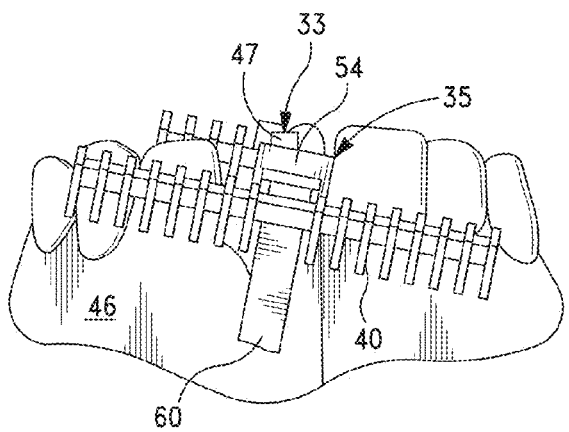
Figure 17:
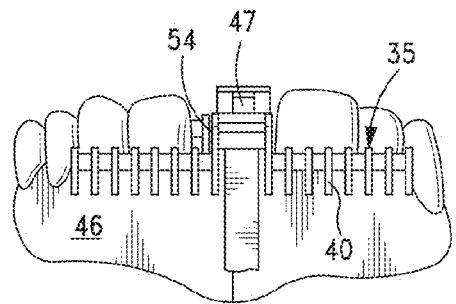
Figure 18:
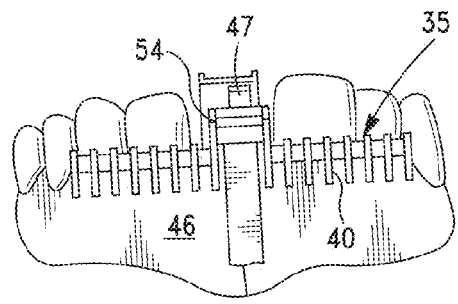

Next, and with reference to FIGS. 15-18, the mounting assembly is adjusted in the MD direction while being fixed in the BL position by the positioning device. As shown in FIGS. 16-18, mounting frame 40 and receiver block 54 may be translated in the MD direction and rotated about an MD axis while resting on the positioning device. Alternatively, the positioning device and/or receiver block may be configured to allow for adjustment of only one of translation and rotation at a time. In an exemplary embodiment, the mounting assembly is translated until it is aligned between the teeth adjacent the edentulous area.

The mounting assembly is then rotated to a desired MD angle about an MD axis extending though receiving hole 53 of the receiver block (see, e.g., FIGS. 16-18). The MD angle adjustment may be aided by the use of reference points on the model. In various embodiments, the mounting frame is configured to aid in MD alignment. In one example, the rails of the mounting frame extend at right angles from the receiver block such that a user can visually determine the angle of the mounting frame from the occlusal plane.

In various embodiments, the MD pivot axis is generally coextensive with the interim receiver block and the upper portion of the positioning device. As noted above, upper portion 42 of the positioning device provides the MD pivot axis of the mounting assembly. The mounting frame rotates about the MD pivot axis while the BL position and BL angle are fixed. Thus, a user only needs to be concerned with adjustment in one direction at a time.

In various embodiments, slot 51 is configured for defining the MD pivot axis of the receiver block. The slot is configured to allow the positioning device to slide up and down in the z-direction, meaning the apical-coronal (AC) direction. In various embodiments, receiving hole 53 is a slot to allow for MD translation of the mounting frame relative to the positioning device.

Figure 19:
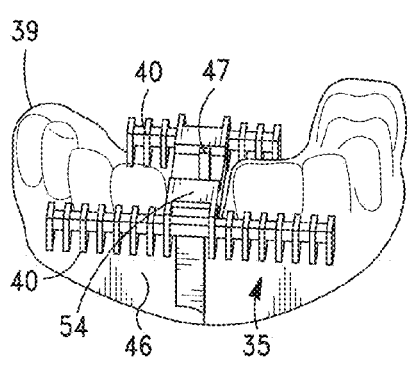
Figure 20:
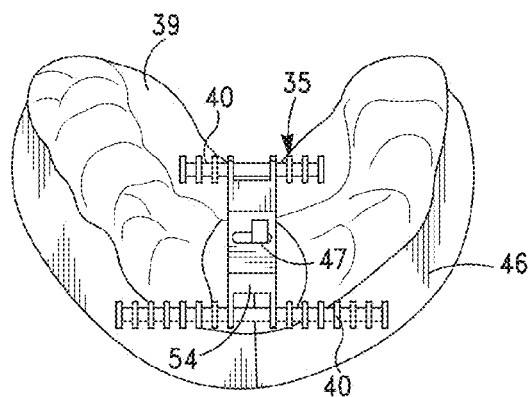
Figure 21:
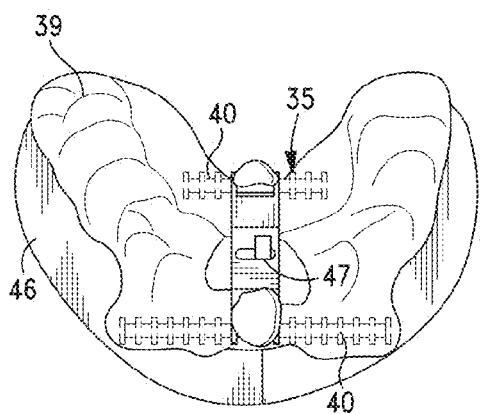
FIGS. 21, 22, 23 and 24 are sequential views illustrating affixing of the mounting frame of FIG. 20 to a template corresponding to the model and the patient's dental arch, forming a mounting assembly, and selection of a rotation block.

Turning to FIGS. 19-21, once the MD position and angle of mounting assembly 35 have been set using positioning device 33 as described above, with the BL position and BL angle of the mounting assembly having been dictated by the tight fitting relationship between the receiving hole 53 and top 42 portion of the positioning device 33, the interim receiver block should roughly be in the desired BL and MD orientation in 3D space. The next step is to fix the mounting assembly position relative to the teeth on the model so the BL and MD positions will not change. In various embodiments, the mounting frame is affixed to the teeth by template 39. The template provides a fixed correlation between the mounting assembly supporting the receiver block and the model, and in particular the patient's dental arch. Suitable materials for the template include, but are not limited to, rigid metals and polymers, thermoplastics, stiff impression material, expandable foam, and adhesives.

In an exemplary embodiment, template 39 is formed by applying orthodontic adhesive (thermoset acrylic) over a portion of the mounting assembly to affix it to the model. The adhesive is allowed to harden thereby forming a rigid template member securing the mounting assembly to the teeth. During the hardening process, the adhesive flows around the model so the hardened adhesive conforms to the teeth contours. The hardened adhesive forms a releasable connection with the model. In this manner, the template allows a user to take the mounting assembly on and off the model with accuracy and repeatability. One will appreciate from the description herein that other template materials and configurations may be used. In various embodiments, the template is a mechanical or chemical fastener.

The discussion thus far has largely focused on the planning phase and the preparation of a preliminary guide assembly constituted by the template, mounting assembly, and interim receiver block. Many aspects of the planning process have clinical consequences and are thus likely to be performed by the same surgeon using the final guide assembly. For example, the positioning of positioning device 33 and mounting frame 40 on the model carry over to the final positioning of the guide assembly in the patient's mouth.

Referring to FIGS. 19-22, after creation of the template, the preparation of exemplary guide assembly 30 moves from the orientation and adjustment phases to creating the final guide assembly. One will appreciate that the above steps, although aiding a user by isolating adjustment to one of BL plane, MD plane, and z-height, generally provide for course adjustment of the guide assembly. For example, the positioning device and mounting assembly have broad range of motion for translation and rotation during the adjustments above. Various aspects of the operations set forth below are directed to fine-tuning the guide assembly for increased accuracy.

Figure 22:
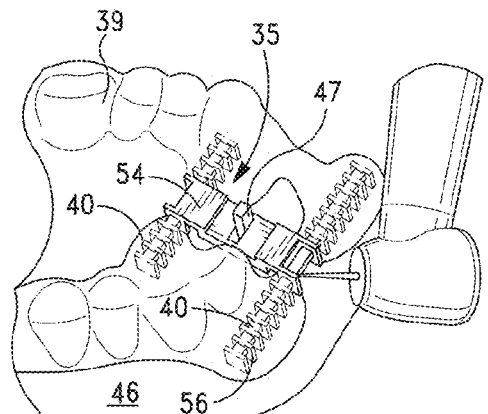

As shown in FIG. 22, interim receiver block 54 is removed from mounting assembly 35. The result is mounting frame 40 fixedly secured to template 39 (see, e.g., FIG. 23). The exemplary mounting frame includes a pair of matching rails 56 attached to the template, which in turn can assuredly affix the mounting frame relative to the teeth. The frame does not include a bridging section spanning over the central portion of the edentulous area and the positioning device, thus allowing significant access to the edentulous area.

Rotation block 37 is then attached to mounting frame 40 of mounting assembly 35. Because template 39 securely supports exemplary mounting frame 40, rotation block 37 can be attached and removed from the mounting frame without affecting or disturbing the mounting frame orientation with respect to the template or to the teeth.

As described above, in various embodiments, the rotation block has a guide hole with a predetermined MD angle. A set of rotation blocks with different MD angles are provided so the user can try the different blocks until the appropriate one is found. The set of rotation blocks may also be provided with different BL angles; however, the adjusting of the positioning device on the model and transfer of information to the mounting assembly as described above generally will obviate or reduce the need for further adjustment in the BL position or angle at this stage.

The desired location of the implant and associated guide trajectory may be determined as would be understood by one of ordinary skill in the art from the description herein. In various embodiments, the guide hole and/or receiving hole are offset by a predetermined distance from a center of the respective block. In various embodiments, the desired implant location is fully inserted into the jawbone such that bone fully surrounds the implant. In other words, the implant is circumferentially covered by bone. In various embodiments, the desired implant location is based on an insertion depth of about 5 mm or more. In various embodiments, the desired location of the implant is based on meeting one or more of the following criteria: about 1.5 mm from the implant to an adjacent tooth, about 3 mm between adjacent implants, and about 1 mm from the implant to the outside surface of the jawbone. The position of the implant may be important to achieve mechanical stability and/or a desired biological reaction.

The use of a rotational block with indexed or fixed positions provides quantifiable positional information. Thus, the user will always know the last position and have the ability to return to the previous position if desired. This also allows the user to move in discrete increments. Further, the rotational block and guide assembly in accordance with the present invention allow the user to adjust alignment in only the desired MD direction while holding alignment fixed in all other directions.

As shown in FIGS. 24, 25, 26 and 27, a drill bit or guide tool is inserted through the selected rotation block while it is mounted to the model to determine if the guide is in the desired position. If the user desires to change the MD angle, a new rotation block may be fixed into place on the mounting frame.

Figure 26:
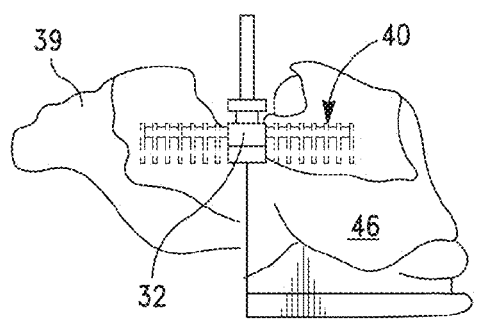
Figure 27:
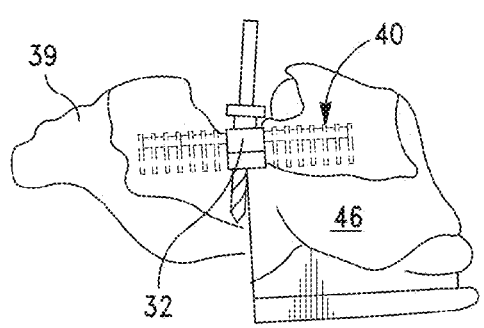
Figure 28:
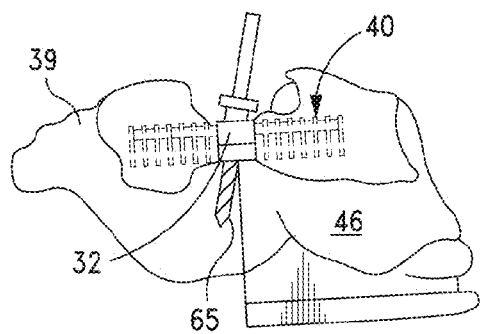

In an exemplary embodiment, the rotation blocks each have a unique MD position to further allow for easy adjustment of MD position. The exemplary rotation block set includes blocks with MD angles of about 0, about 3, and about 7 degrees, as shown in FIGS. 26, 27 and 28, respectively. The exemplary rotation blocks are also configured to be flipped over (e.g., rotated 180° relative to a vertical axis) and fixed onto the frame such that about −3 degrees and about −7 degrees may also be achieved.

One will appreciate that the rotation block and mounting frame may be modified to increase or decrease the adjustment possibilities and precision. For example, it may be desirable to allow for finer adjustment of the MD angle. In various embodiments, the rotation block includes a guide hole configured to allow for minute, controllable adjustments in one or more directions for fine-tuning.

Although installation of the rotation block is described as occurring on the model, one will appreciate that substitution of the interim receiver block with a selected rotation block may be performed after the guide assembly has been transferred to a patient's dental arch. The exemplary mounting frame includes a snap fastener so a user receives tactile feedback confirming the rotation block is fixed into place thereby reducing the risk of parts falling into the patient's mouth.

After selection of a rotation block, guide assembly 30 (including mounting frame 40 and rotation block 37) with template 39 is transferred from the model to a patient's dental arch. The rotation block is generally connected to mounting frame 40 at or near the BL pivot point of the mounting frame (corresponding to BL pivot hole 63). As illustrated in the figures and described above, the mounting frame mounts to the outer surface of the teeth, which enables rotation block 37 to be mounted in the general edentulous area just above or adjacent to the jawbone. The rotational axis point of the guide hole in the rotation block is lower in comparison to conventional guide devices. This tends to increase precision of the orientation process because rotation of the guide hole results in a relatively minimal consequent translation in the BL and MD positions.

Mounting frame 40, template 39, and selected rotation block 37 together form the assembled surgical guide 30. The assembled surgical guide is ready for transfer to a patient. As described above, the template and mounting frame are configured to accurately and precisely transfer the position from the model to the patient's dental arch. The mounting frame is removed from the model and the guide is transferred to the patient's dental arch.

The patient's dental arch should correlate to the model used previously; however, variations do occur occasionally. Therefore, it may be necessary to make further adjustments. In this case, the rotation block may be replaced with a new rotation block while the template and mounting frame are positioned in the edentulous area of the patient's dental arch. In various embodiments, the guide assembly is configured to allow for fine adjustment of the rotation block. In one example, the rotation block allows for adjustment of one or more of the BL position, MD position, BL angle, MD angle, and z-height of the rotation block through a narrow range of motion. In some cases it may be necessary to adjust the position of the mounting assembly after the rotation block has been selected. One will appreciate from the foregoing that a user may adjust the dimensions and configuration of the mounting frame—e.g. by cutting, shaving, shimming, and the like—to fine-tune the ultimate position of the mounting frame. The mounting frame may also be configured to allow for additional fine adjustments, for example, by including a slot for MD translation of the rotation block.

The final position is set by securing the mounting frame in position using adhesives, fasteners, or similar methods.

Figure 31:
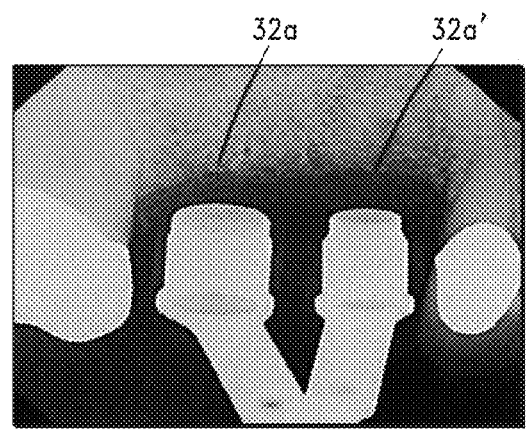
FIG. 31 is an X-ray of the patient's mouth after a radiographic implant has been implanted into the jawbone using the dental guide system of FIG. 29.

A radiographic implant replica (RIR) may optionally be used after any of the steps above to verify the alignment and orientation of the guide assembly (see, e.g., FIG. 31). The RIR acts as a visual marker in a CT scan or X-ray.

To summarize the exemplary method for preparing a guide assembly described above, the method starts with a model representing a patient's dental arch and proceeds with preparing a guide assembly for guiding a dental implementation in the arch and jawbone of the patient. The model is used to determine the relative positions of the teeth, jawbone, and tissue depth. A positioning device is aligned with a trajectory for the dental implementation and determines the BL position, z-height, and BL angle. A mounting frame assembly is adjustably secured to the positioning device via a receiver block such that the BL position, z-height, and BL angle are transferred, in general, from the positioning device to the mounting assembly. The MD position and MD angle of the guide hole for receiving the dental implementation are then adjusted by moving and rotating the mounting assembly about an upper portion of the positioning device. The BL and MD course adjustments are then set by creating a template to fix the mounting assembly in place. The receiver block is then replaced with a rotation block having a selected trajectory angle to fine-tune the MD and/or BL angle. The resulting mounting assembly and template embody the orientation information and enable transfer to a patient's dental arch corresponding to the model. The template allows for easy removal from the model and snapping into an accurate and precise position in the patient's mouth. Optional fine adjustments may then be made to achieve a more accurate surgical guide orientation.

Figure 34:
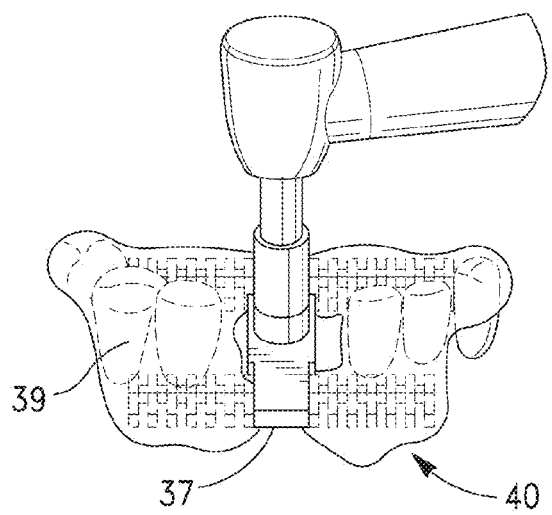
FIGS. 34, 35 and 36 are sequential views of an upper jaw of a patient's mouth, illustrating the method for performing an exemplary osteotomy and subsequent placement of an implant using the dental guide system in accordance with the present invention.
Figure 35:
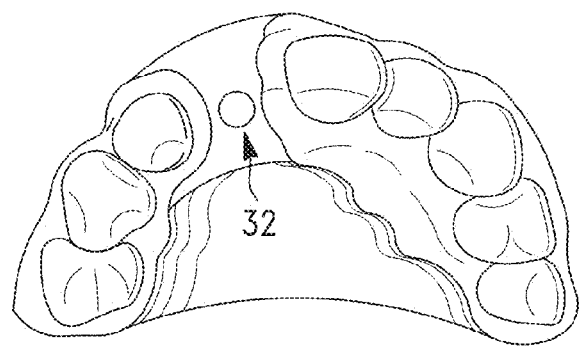
Figure 36:
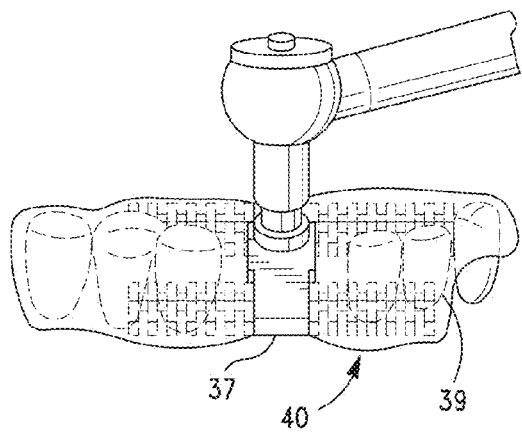

The use of exemplary surgical guide assembly 30 in accordance with the present invention can now be described. Turning to FIGS. 34-36, the surgical guide assembly is positioned in a patient's dental arch. The guide assembly includes rotation block 37 with guide hole 44. The surgical guide assembly is secured in the patient's mouth so the guide is rigidly fixed relative to the dental arch. The guide assembly bridges the edentulous area such that the rotation block and guide are generally positioned immediately above the jawbone and tissue. In an exemplary embodiment, the site is prepared prior to attaching the surgical guide as would be understood by one of skill in the art from the description herein. The preparations may include punching a hole in the tissue and cutting soft tissue away from the desired site (as shown in FIG. 35).

The exemplary guide includes a hole 5.05 mm in diameter. A drill bit 65 is inserted through guide hole 44 of the rotation block and directed to the jawbone. A user then activates the drill to create a hole in the jawbone for receiving an implant while the drill bit is held in position by the guide assembly. The guide is sufficiently rigid to maintain a trajectory of the drill bit in the jawbone during the drilling operation.

The drill bit is then removed from the drill guide. In some cases, the guide assembly is removed from the patient's mouth and the jawbone and surrounding tissue are given time to heal. Alternatively, it may be desirable to place the implant during the same visit as the osteotomy.

The guide assembly is positioned over the dental arch again. The implant (abutment) is inserted through guide 44. If the implant is smaller than the guide hole 44, an adhesive or other material may be used to secure the implant in the guide.

As the orientation of guide hole 44 has been maintained in each step of the process, the implant will be easily directed into the hole created in the jawbone. This reduces the risk of the implant being delivered off-center from the hole in the jawbone.

Figure 37:
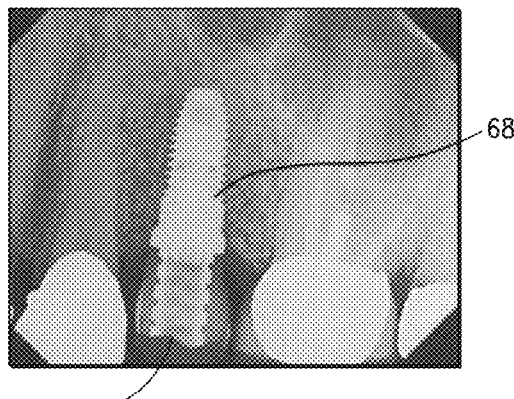
FIG. 37 illustrates the correlation of the top of the implant to the edge of the jawbone, pivot point of the positioning device, and crown of adjacent teeth.
Figure 38:
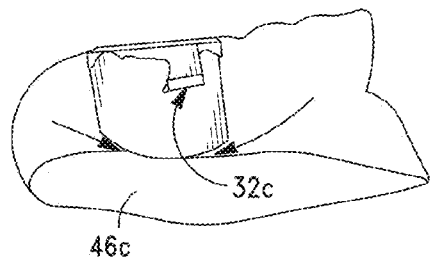
FIGS. 38-39 illustrate a CAD model similar to that of FIGS. 5-28 for positioning a guide assembly in accordance with the present invention.
Figure 39:
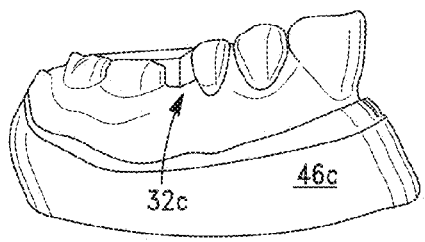

FIG. 37 is an X-ray of a jawbone after use of the guide assembly as described above. The X-ray illustrates placement of an implant 67, also referred to as abutment, in a jawbone of a patient. The implant may be formed from a variety of materials including, but not limited to, titanium, surgical stainless steel, and gold. The top of the inserted implant is in-line with a top of the jawbone and slightly below the top of the soft tissue.

After the implant has been placed, an exemplary prosthetic tooth 68 is positioned on top of the positioned implant. The prosthetic is attached to the implant by conventional means, such as a screw fastener. The exemplary screw is tightened to a predetermined torque to avoid stressing the implant or having the prosthetic loosen. In various embodiments, implant 67 and/or prosthetic 68 comprises white zirconia to better complement the aesthetics of a dental implant restoration. In some cases, it may be desirable to perform one or more of the above operations in the same visit.

Figure 29:
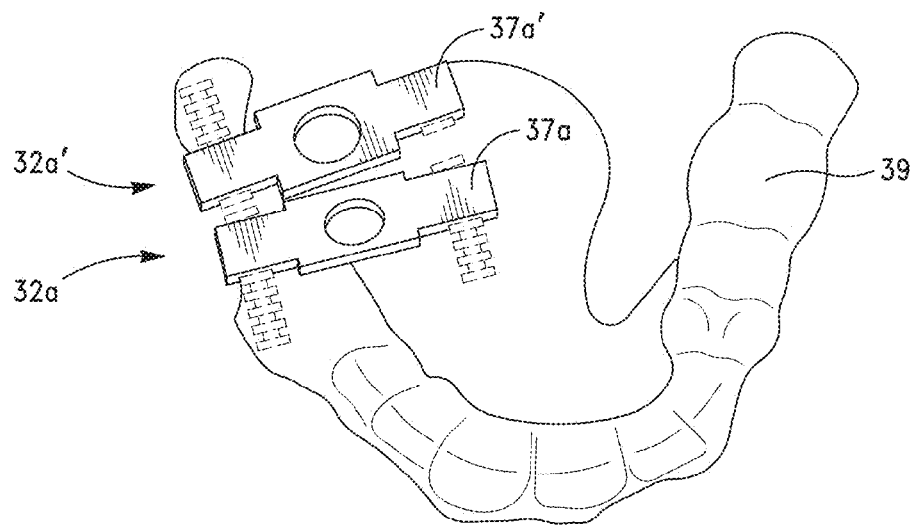
FIG. 29 is a bottom view of a dental guide system similar to that of FIG. 1 positioned over a patient's dental arch corresponding to a model, illustrating use of two rotation blocks with different positions in accordance with the present invention.
Figure 30:
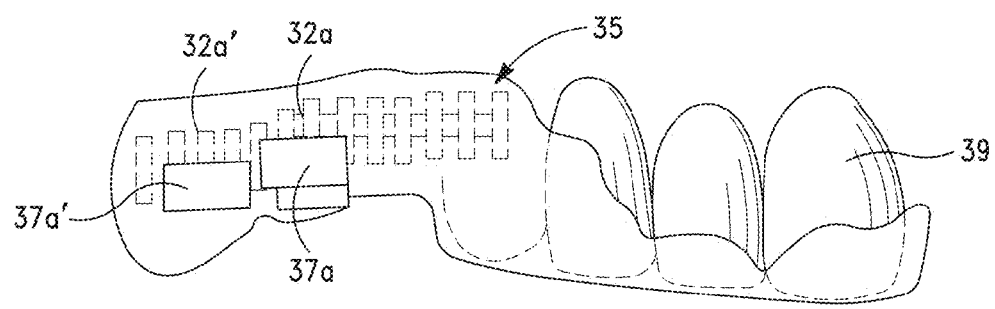
FIG. 30 is a side view of a patient's mouth with the dental guide system of FIG. 29 positioned along the dental arch in the region of the edentulous area.

In another embodiment of the present invention, a surgical guide assembly 30a is similar to guide assembly 30 described above but includes two rotation blocks as shown in FIGS. 29-31. Like reference numerals have been used to describe like components of the guide assembly.

Surgical guide assembly 30a is prepared similar to surgical guide assembly 30 except that two positioning devices are used. The model is prepared by cutting along a first edentulous area 32a and then removing a second section corresponding to a second edentulous area 32a'. A first positioning device is aligned as described above in the first edentulous area. Next the second section is placed back on the model with the first positioning device in a sandwich configuration. The second positioning device is then aligned on an opposite side of the second section. The whole model is then reassembled and one or more mounting assemblies are positioned and aligned on the two aligned positioning devices. The aligned mounting assemblies are then fixed using one or more templates. The final guide assembly is assembled by selecting rotation blocks for each edentulous area.

In operation and use, guide assembly 30a is used in substantially the same manner as guide assembly 30 discussed above. FIG. 31 illustrates a patient's dental arch after two implants have been placed in the jawbone using the surgical guide assembly.

Figure 32:
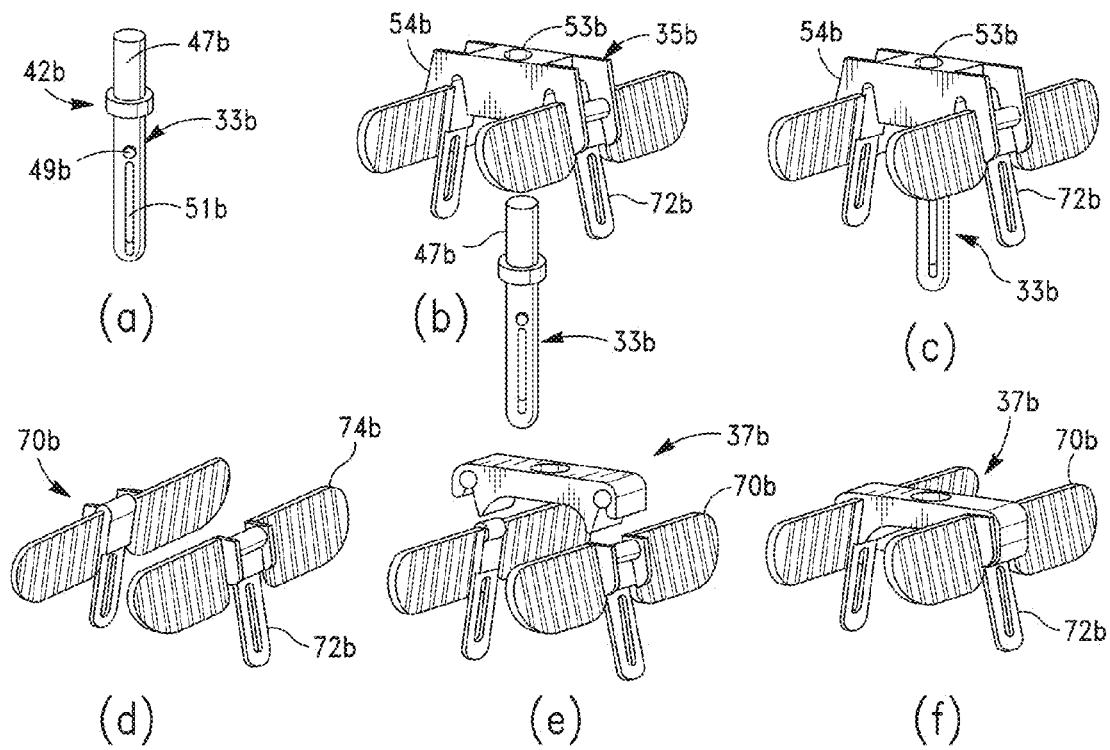
FIGS. 32(a)-32(f) are sequential views illustrating stepwise assembly of a guide system similar to that of FIG. 1.
Figure 33:
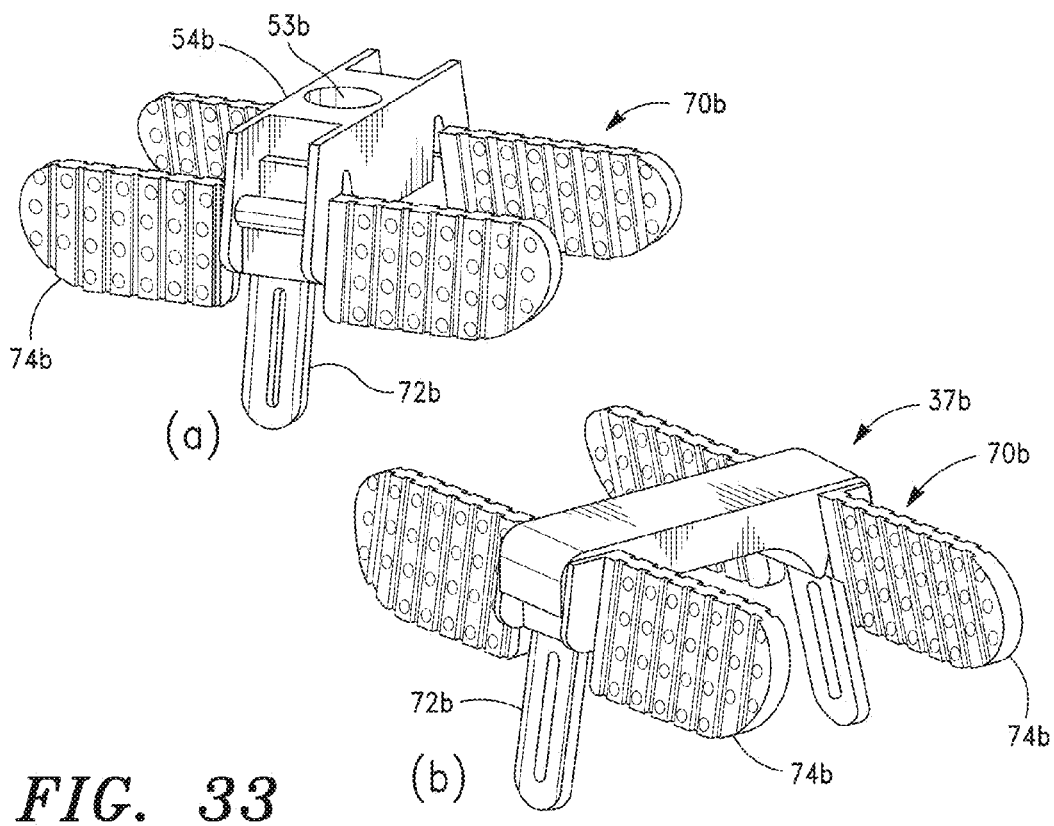
FIGS. 33(a) and 33(b) are perspective views of the guide system of FIG. 32.

In another embodiment of the present invention, a surgical guide assembly 30b is similar to surgical guide assembly 30 described above but includes a different mounting assembly 35b as shown in FIGS. 32-33. Like reference numerals have been used to describe like components of guide assembly 30b. Mounting assembly 35b includes a mounting frame 40b supporting an interim receiver block 54b (shown in FIG. 33(a)) or rotation block 37b (shown in FIG. 33(b)).

The frame is formed of a pair of wing members 70b. Each wing member has a central portion 72b and flap portion 74b. The central portion extends in a z-direction for engaging tissue below the edentulous area and BL alignment. The flap portion has a flat surface for promoting engagement with adjacent teeth.

Rotation block 37b attaches to mounting frame 40b similar to rotation block 37. Upper ends of each of the central portions have a tab configuration for engagement with hook members at each end of the rotation block so the block can be snapped and released. Mounting frame 40b is otherwise used in a similar manner to mounting frame 40.

One will appreciate that the planning and preparation of the guide assembly may be carried out in other fashion. In various embodiments, a CAD model 46c is used in place of a physical dental cast model 46. Referring to FIGS. 38-43, a method of preparing a surgical guide in conjunction with a computer system and the apparatus of the present invention is shown. Like reference numerals have been used to describe like components of the guide assembly.

In many ways model 46c is prepared and used similar to model 46 to form the ultimate guide assembly. The patient's mouth is surveyed and mapped on a computer. The computer may run specialized software that allows the user different 2D and 3D views of the mouth and teeth. Various software packages are available which provide a multitude of features for implant planning. An exemplar of such a computer application is NobelProcera™ sold by Nobel Biocare of Zurich, Switzerland. One will appreciate from the description herein that the software application may be customized in accordance with the present invention.

Figure 40:
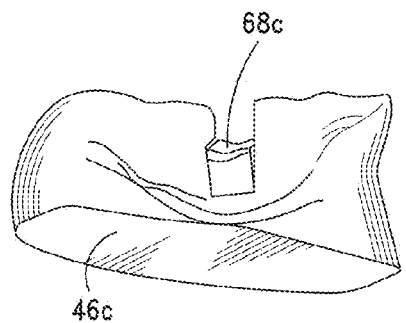
Figure 41:
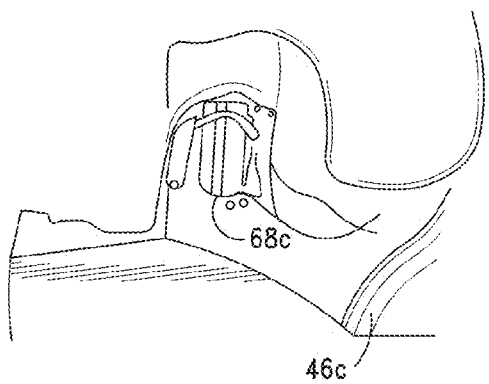
Figure 42:
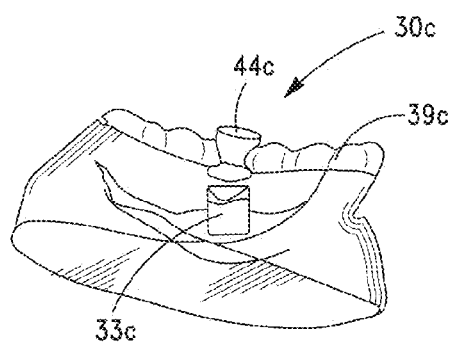
Figure 43:
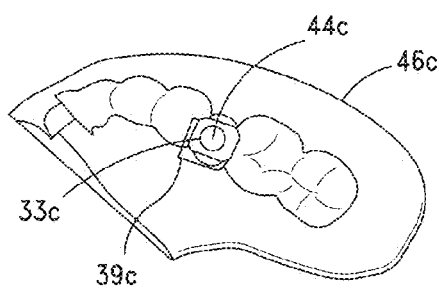

In various embodiments, all the above steps from creation of the model to alignment of the mounting assembly in the BL and MD planes are performed on a computer similar to the physical model-based method described above. The software may be loaded with data representing the various guide components such that the positioning and alignment of both the positioning device and mounting assembly can be virtually performed using the CAD model. Model 46c is used to determine the region of the edentulous area and relative position of the jawbone and soft tissue (e.g. FIGS. 38 and 39). The desired location of the implant relative to the model is then determined as shown in FIG. 41. Next, the locations of a virtual implant and surgical guide assembly 30c are determined based on the desired location of the implant (shown in FIGS. 42 and 43). Surgical guide assembly 30c corresponds to mounting assembly 35 and rotation block 37. The adjustment of the position of guide assembly 30c may be carried out in a similar fashion to the operations described above. In various embodiments, the BL position is fixed, followed by the BL angle and then the MD positioning. In the exemplary embodiment, the BL adjustments are performed first (e.g. FIGS. 40-41). As shown in FIG. 40, the tissue depth and jawbone location can be verified during the positioning. After the BL adjustments are made, the MD position and angle are adjusted as shown in FIGS. 42-43. The computer is configured or programmed to allow adjustment in one direction or angle while holding the other positions and angles fixed.

Guide assembly 30c includes a guide bore 44c for receiving a dental tool, implant, or prosthetic. Guide bore 44c corresponds to guide bore 44 of rotation block 37. The virtual guide bore is mounted on virtual rails which are configured for attaching to the model teeth. The guide assembly is positioned on the CAD model in a similar manner to positioning device 33, mounting frame 40, and rotation block 37. The CAD software may be used to illustrate a location of an implant and prosthetic tooth 68c based on the guide assembly positioning.

After the positioning is complete, a virtual template 39c for fixing the guide assembly in position is mapped on the digital model. A guide assembly is then fabricated from the model data. In various embodiments, the computer software and/or applications create a data file (e.g. a STL or DWG file extension) which embodies a three-dimensional (3D) object from which a computer-aided model (CAM) may be produced. The computer data may then be used to manufacture a physical guide assembly 30c and template 39c using conventional manufacturing tools.

Figure 43A:
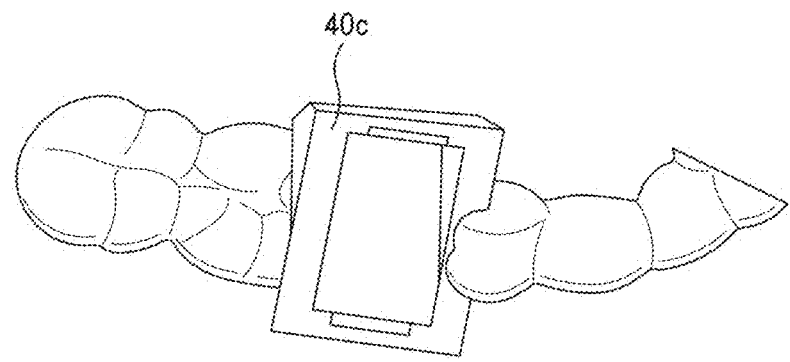
Figure 43B:
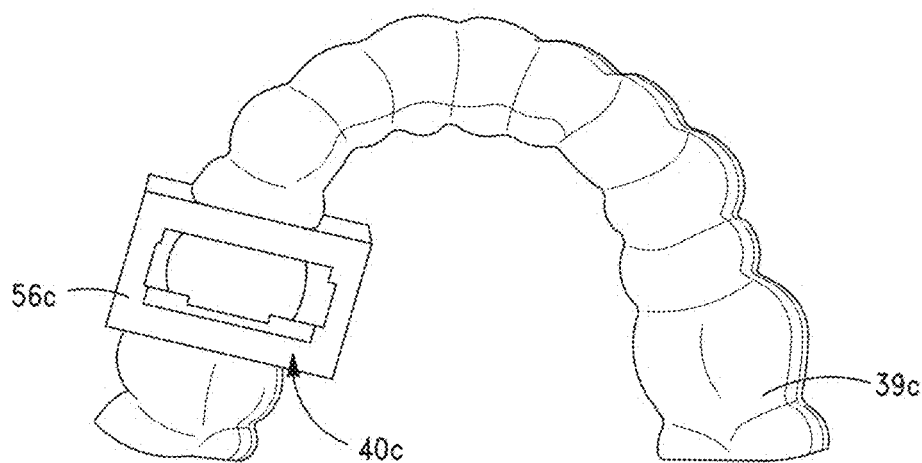
Figure 43C:
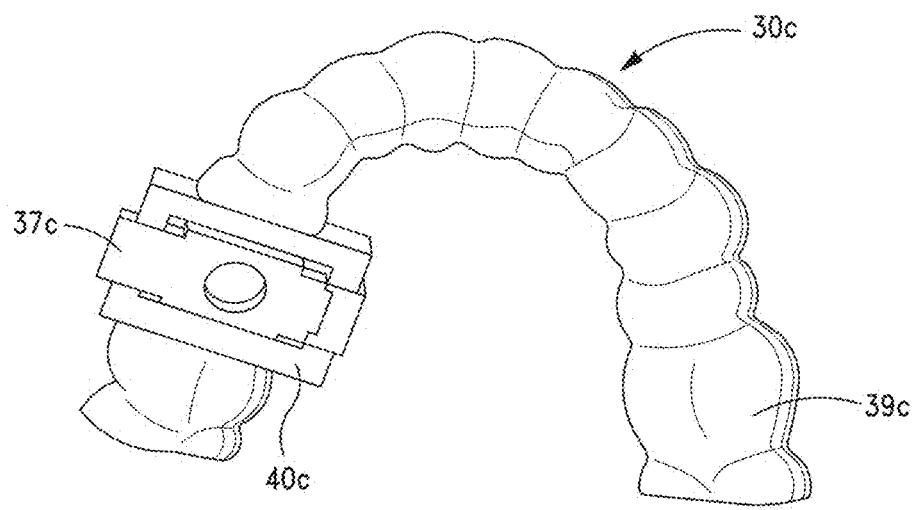
Figure 44:
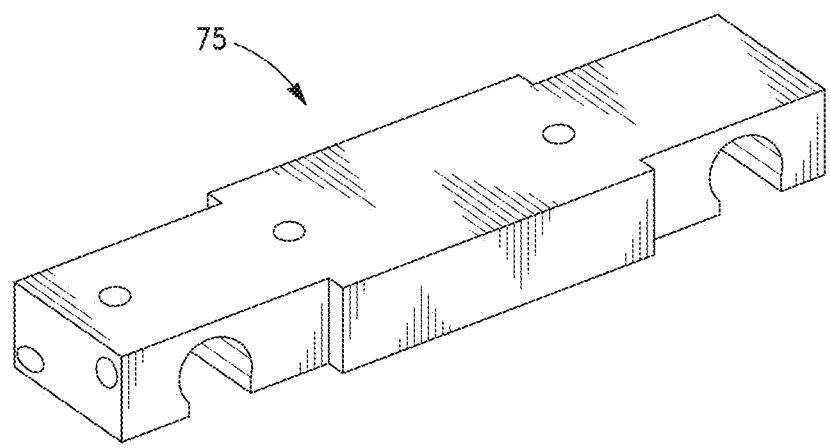
FIG. 44 is a perspective view of a guide insert similar to the rotation block of FIG. 1 in accordance with the invention.
Figure 45:
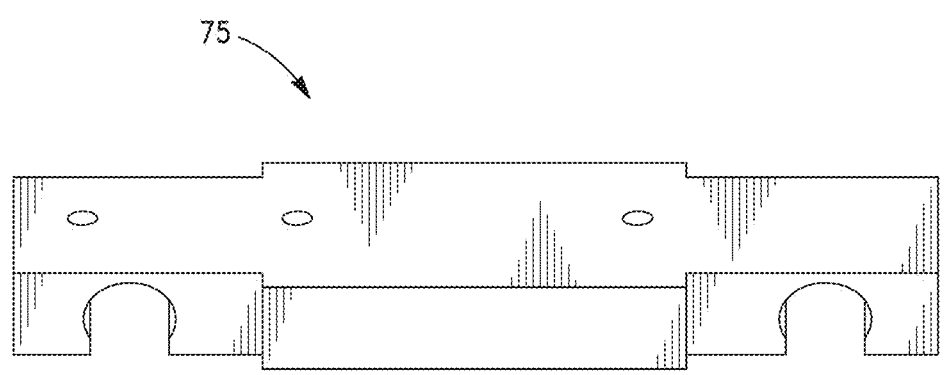
FIG. 45 is a side view of the guide insert of FIG. 44.
Figure 46:
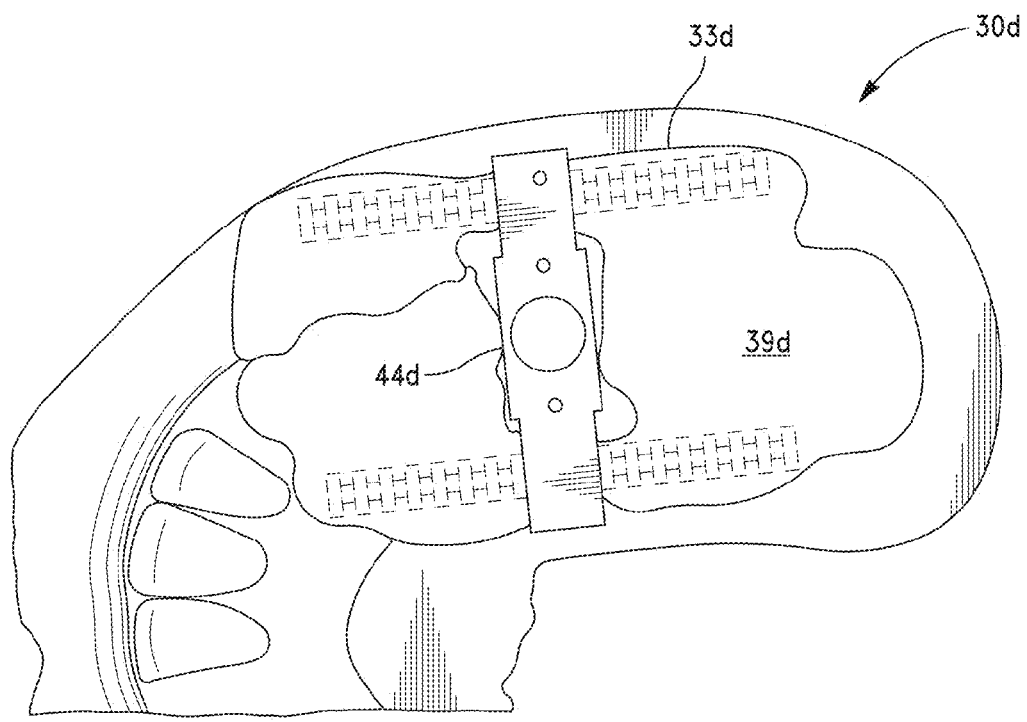
FIGS. 46 and 47 are top views of a dental guide system in accordance with the invention, illustrating mounting of the guide insert of FIG. 44 on the mounting assembly of FIG. 23 to form the dental guide system.
Figure 47:
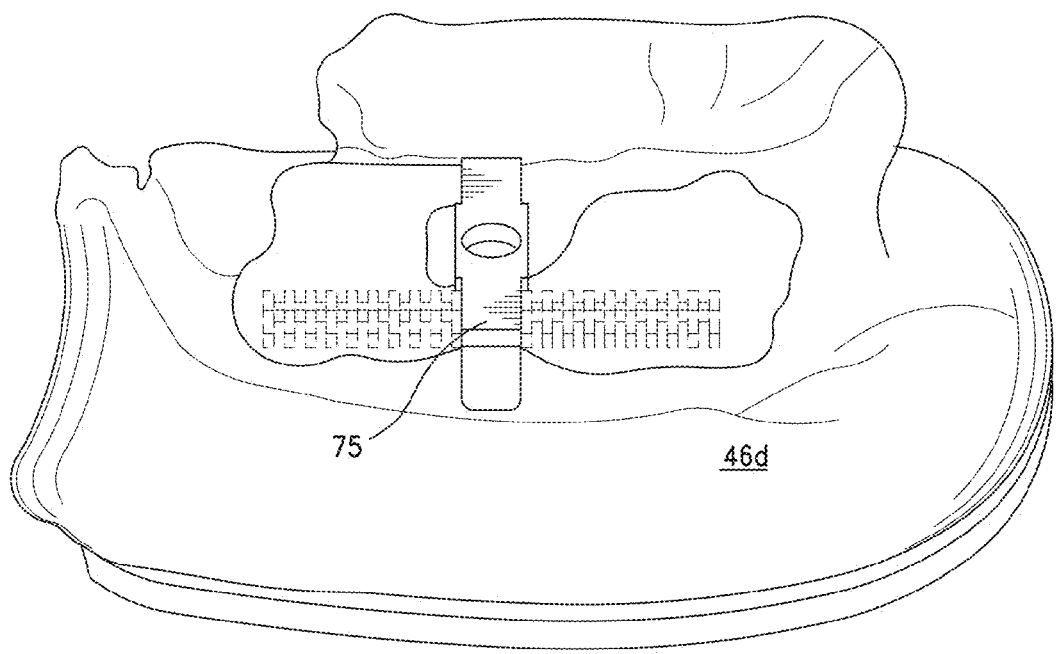

FIG. 43A illustrates a computer model embodying the adjustment information. A physical object can then be fabricated from the computer-based model as shown in FIG. 43B. In an exemplary embodiment, the physical object is manufactured using stereolithography. In the exemplary embodiment, the computer-based object and corresponding physical object includes retentive rails 56c similar to mounting frame 40. An exemplary rotation block 37c can then be snapped onto the rails of the frame. Rotation block 37c can be selected in a manner similar to rotation block 37. A user can add and remove various rotation blocks from a kit until a rotation block is identified that provides the desired guide trajectory. Alternatively, the rotation block can be selected or adjusted on the computer and fabricated as a custom piece that is then assembled to the mounting frame.

One will appreciate that computer modeling can be used in place of any of the physical steps up to the fabrication of the guide assembly with or without the rotation block. In other words, such computer modeling may be used in place of any or all of the physical steps described above using the digital model such as initial alignment of the mounting assembly to model 46c.

With reference to FIGS. 44-47, another guide assembly 30d similar to guide assemblies 33a and 33c is shown. Guide assembly 30d includes a guide insert 75 manufactured based on a computer planning process. The guide insert largely corresponds to rotation block 37 except that guide insert 75 is a customized part. Adjustments are made on a computer such that the final guide assembly product does not require further course adjustments. The guide assembly, however, may optionally be configured to allow for fine adjustments.

Figure 23:
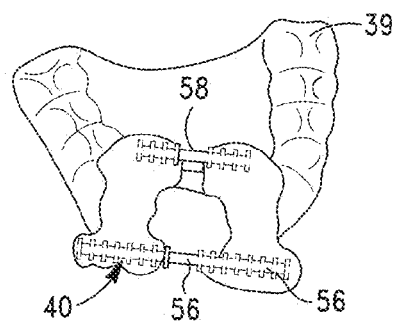
Figure 24:
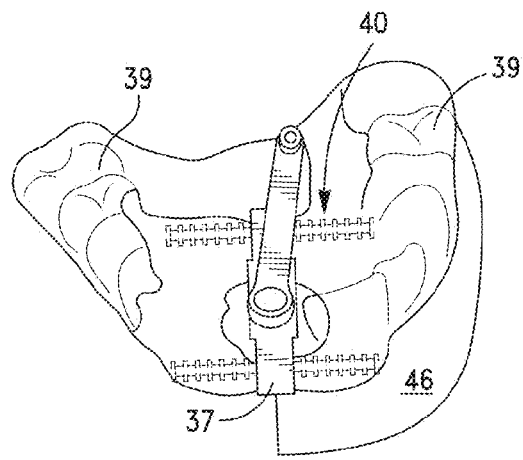
Figure 25:
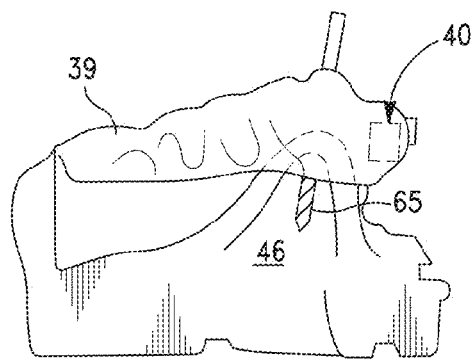
FIGS. 25, 26, 27 and 28 are sequential views illustrating insertion of a dental drill through the assembled guide system of FIG. 24 in accordance with the present invention, illustrating a trajectory of the drill bit in the MD and BL planes.

The guide insert is configured to attach to the rails or template 39 (shown in FIG. 23). The exemplary guide insert 75 is dimensioned to extend across the space from rail 56 to rail 56. The guide insert includes a guide bore 44d which corresponds to guide bore 44 of rotation block 37.

The planning and fabrication of exemplary guide insert 75 and guide assembly 30d proceeds similar to guide assembly 30 described above. A physical dental cast model or virtual model is constructed based on the patient's dental arch. The BL position, BL angle, and z-height for the final guide assembly are determined using positioning device 33, freehand positioning, or computer-based techniques. Next, mounting frame 40 is positioned on the model. The general BL and z-height information for the guide insert are determined from the mounting frame position on the model.

After the mounting frame is set in position, the user vacuforms a template 39d to the model. The exemplary template is cut to provide space in the edentulous area for the eventual guide assembly.

Next, rails 56 (shown in FIG. 23) are fixed to template 39d to form an interim guide assembly 30d on model 46d. Guide insert 75 is fastened to the template to complete the interim guide assembly similar to the assembly shown in FIG. 13. A user next sets the MD position and MD angle using the interim guide assembly in a manner similar to that described above and shown in FIGS. 15-22. After completing the position, the guide assembly is fixed to the model using an adhesive or other means. Unlike guide assembly 30, however, after the template is assembled, most aspects of the planning process for guide assembly 30d are performed on a computer.

As will be appreciated from the discussion below, the BL positioning of the template does not need to be as accurate with the technique described herein because further adjustments can easily be made on the computer. Moreover, the tissue depth does not need to be determined using the computer-based technique because the tissue and bone depth can be determined with sufficient accuracy from the scan image.

The following planning process involves matching the patient's dental information to the guide assembly. A user fits the exemplary guide insert onto the template. In the exemplary embodiment, the guide insert is configured to snap onto the vacuformed rails 56 of the template (shown in FIGS. 23-24) similar to rotation block 37.

All or a portion of guide insert 75 includes a marker material such as radiographic material. The exemplary guide includes a radio-opaque insert for imaging in a computerized tomography (CT) scan or X-ray. In various embodiments, the guide insert includes two markers (e.g. radiographic markers) such that angular information can be obtained from the resulting image. Generally the markers should be at least about 0.5 mm apart to obtain acceptable accuracy for matching to the computer model information. In various embodiments, substantially all of the guide insert is formed of material identifiable by the scan such that the positional information can be obtained from the surface data instead of radiographic inserts and the like.

The assembled template is then placed in the patient's mouth and a scan is taken. A software program processes the scan information to create a 3D computer model. Exemplary software packages include NobelGuide™ sold by Nobel Biocare, iGuide sold by iDent, and SimPlant® by Materialise. One will appreciate that the above model-based process is omitted entirely. In various embodiments, the method of forming the guide assembly starts with taking a scan of the patient's mouth and the guide assembly is designed entirely in virtual space. For example, the mounting assembly and guide insert may be modeled on the computer.

The computer is preloaded with data related to the guide insert so the insert can be superimposed into the 3D model representing the patient's mouth. Based on information about the insert and template, the software can accurately determine the position of the insert based on the location of the radiographic material in the insert. The position of the template on the teeth can then be derived from the insert position information.

Once the computer model has been constructed with the guide insert, the implant planning phase can proceed. A virtual guide hole is created in the guide insert computer model. The positioning of guide insert 75 is performed in a similar manner to the process described above. Although the BL position, BL angle, and z-height are largely fixed at this stage, small adjustments can be made if necessary. In various embodiments, the desired implant location is at an insertion depth of about 5 mm or more. With the exemplary guide insert, the desired implant location is about 9 mm below the guide bore. The exemplary system includes computer memory for storing information related to the surgical guide and its position at various steps in the process.

After determination of the final position for guide insert 75, the final guide insert product can be fabricated. The guide insert can easily be fabricated using the computer data. Exemplary guide insert 75 is fabricated by stereolithography. Other conventional techniques may be used including, but not limited to, printing and other rapid prototyping techniques, computer numerically controlled (CNC) machining, milling, and injection molding. In various embodiments, the guide insert is milled in the dental office. Suitable machinery for milling or machining include those sold by Sirona and Henry Schein®. The customized guide insert may be manufactured by a vendor or fabricated in the lab by a dental practitioner.

By contrast to rotation block 37, guide insert 75 is a custom-designed and fabricated piece with a fixed guide bore alignment. One will appreciate that the user has greater positioning flexibility during the planning process with the computer-based method. Accuracy may also be increased. The guide insert fabrication can also be a hybrid technique making use of the customized guide insert while realizing cost efficiencies and other advantages of prefabricated rotation blocks. For example, the guide insert may be fabricated by conducting the planning on a computer and then forming a guide bore in a prefabricated insert or rotation block using the computer-based planning information.

To create guide assembly 30d, a user removes the interim guide insert from the template and attaches the final guide insert derived from the computer model. As computer modeling involves an accurate transfer of information from the patient's mouth to the computer and into the final insert product, the guide bore position ultimately will be in the desired position within an acceptable tolerance range. Nonetheless, fine tuning of the position may be accomplished, if desired, similar to final positioning of the assembly with a selected rotation block.

In this manner, guide assembly 30d largely realizes many of the advantages of a customized product without the associated commensurate costs and increased fabrication times. As discussed above, the planning and fabrication process afford a user a large degree of flexibility and choices. For example, the dental practitioner can choose whether to perform most of the fabrication and assembly of the customized product in the office or contract the work with a vendor. Many of the implant planning steps may also be performed on the computer instead of in a lab.

Figure 48:
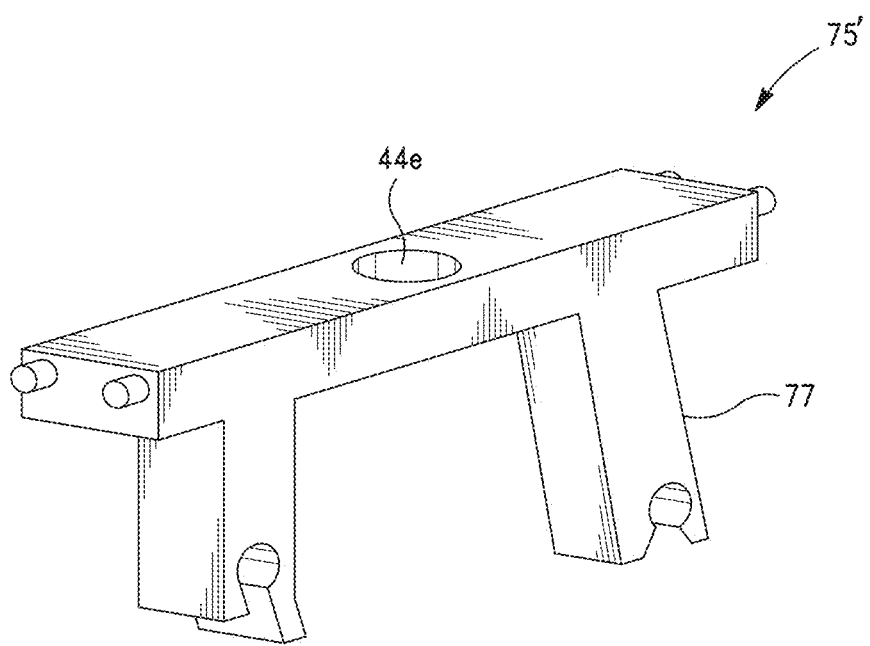
FIG. 48 is a perspective view of another guide insert for use with the guide system of FIG. 1 in accordance with the present invention.

Turning to FIG. 48, a guide insert 75' for use with template 39 (shown in FIG. 23) is shown. Guide insert 75' is similar to guide insert 75 but includes downwardly-extending arms 77 with grooves for attaching to the template. In contrast to guide insert 75 and rotation block 37, the top portion of guide insert 75', which includes guide bore 44e, extends above the occlusal plane of the teeth. With traditional scanning techniques, there can be problems with scatter below the occlusal plane. For example, fillings and other materials and apparatus can cause imaging problems. Because guide insert 75' is positioned above the occlusal plane, a better scan image can be achieved. The positioning and fabrication of guide insert 75' is performed similar to that of guide insert 75.

Figure 49:
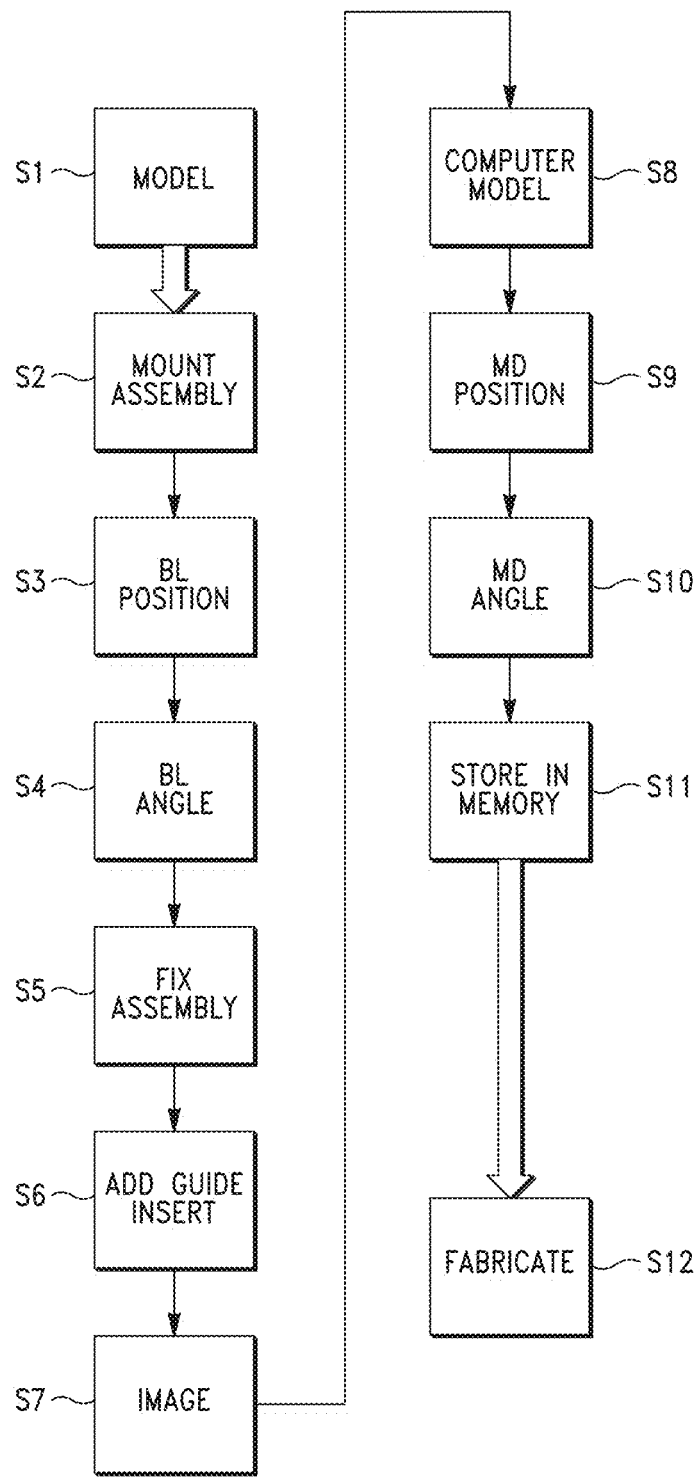
FIG. 49 is a flowchart of the method of preparing the surgical guide for positioning a dental implementation in accordance with the present invention.

FIG. 49 illustrates the steps for preparing a surgical guide in accordance with various aspects of the invention. In S1, the patient's mouth is surveyed and a model is created based on the patient's mouth. The model may be a physical model or a computer-based model. The exemplary model is a computer model.

Next, the BL position of the guide assembly is planned in a manner similar to that described above. In S2, a mounting assembly is mounted to the model. The jawbone region is determined as discussed above, and the mounting assembly is positioned relative to the jawbone region and edentulous area. In S3, the mounting assembly is positioned in a desired BL position. The exemplary BL position is in-line with the jawbone region. The mounting assembly is also positioned in the z-axis in S3. In various embodiments, the z-axis and BL positioning are performed essentially simultaneously. In the exemplary method, the z-axis positioned is performed sequentially with the BL positioning. Next, in S4, the BL angle is adjusted and fixed.

In S5, the mounting assembly is fixed in position. In the exemplary method, the BL position, BL angle, and z-depth of the mounting assembly are fixed by mechanical means such as by application of a dental adhesive or fasteners.

In S6, a guide insert is attached to the guide assembly thereby forming an interim guide assembly. The guide insert includes a guide hole corresponding to a dental implementation. In an exemplary embodiment, the guide insert is attached to the guide assembly before it is attached to the model or before fixing the BL position and/or z-depth of the mounting assembly. The exemplary guide insert is formed of a material capable of being imaged with a CT scan or X-ray. One will appreciate that the guide insert may be attached in a manner similar to rotation block 37.

In S7, the surgical guide is imaged on the patient's dental arch. In the exemplary method, the surgical guide is X-rayed in the patient's actual mouth. The X-ray information is superimposed onto an image of the patient's mouth in the computer, which is obtained from the initial X-ray or CT scan. The computer model includes virtual objects corresponding to the guide assembly. Optional S8 includes creating a computer model based on information related to the position of the interim guide assembly, including the guide insert. Conventional imaging software and technology may be used as will be appreciated from the description herein.

Optional S9 is MD positioning of the interim guide assembly on the computer model. The exemplary MD positioning is performed entirely on the computer. The MD position may be determined as will be understood by one of skill in the art. Unlike conventional techniques, however, the MD position can be adjusted and checked easily because it is computer-based. Additionally, because the BL position has already been set, the MD positioning can be done independently. Next, the MD angle is determined in S10.

By step S11, the z-depth, BL position and angle, and MD position and angle have been accurately determined. In optional S11, information related to z-depth, BL position, BL angle, MD position, MD angle, and a combination thereof is stored in the computer memory.

The final step, S12, is to fabricate a physical guide assembly based on the model information in the computer.

Figure 50:
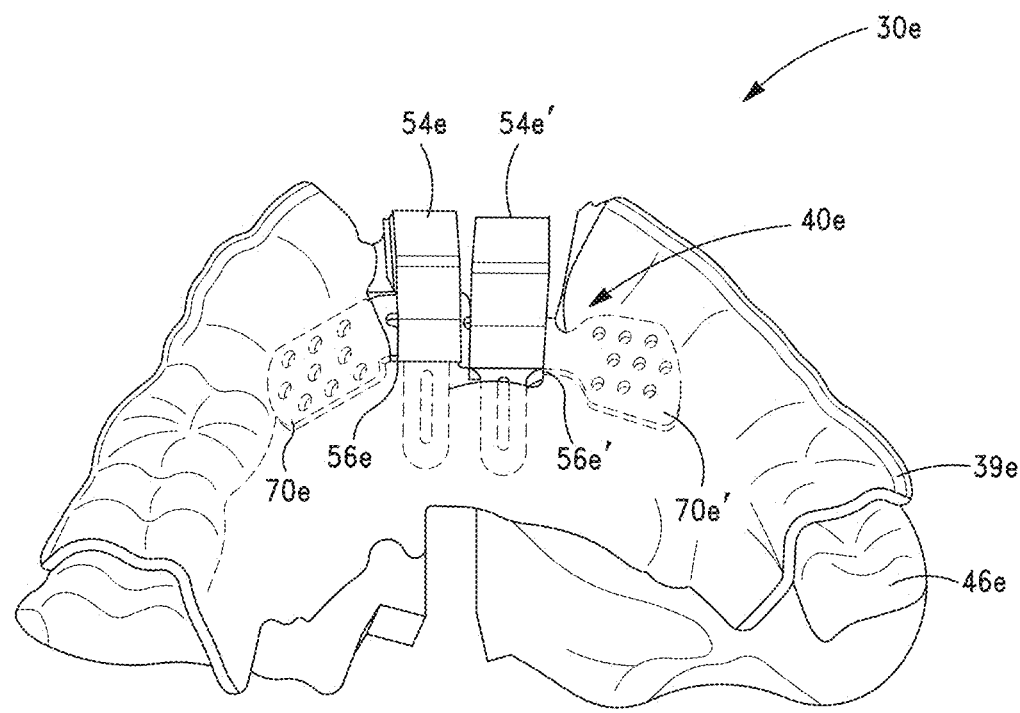
FIG. 50 is a back view of a guide system similar to that of FIG. 1, illustrating use of two mounting assemblies and a radiographic marker in accordance with the present invention.
Figure 51:
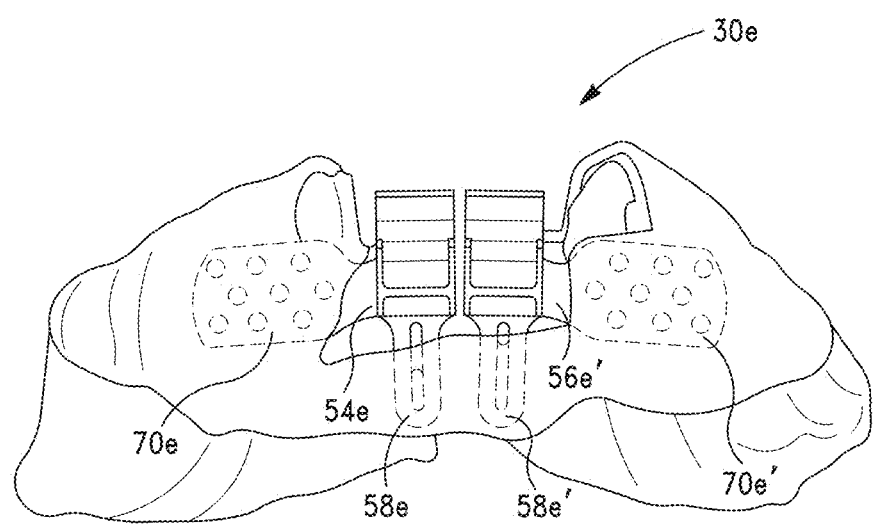
FIG. 51 is a front view of the guide system of FIG. 50.

Turning to FIGS. 50-53, another guide assembly 30e similar to guide assemblies 30a, 30b, 30c, and 30d is shown. The exemplary guide system includes two guide assemblies 30e and 30e'. In many respects, each guide assembly 30e is similar to guide assembly 30b and includes a mounting frame 40e having rails 56e for attaching an interim receiver block 54e and subsequently a rotation block 37e. Wing portions 70b extend from the rails for grasping the teeth and model. Guide assembly 30e is generally assembled similar to guide assembly 30 with the additional step of cutting one rail section from the assembly so it can be mounted side-by-side with the other guide assembly as shown in FIGS. 50-51.

Rotation blocks 37e are positioned and selected similar to rotation block 37 except that each guide assembly 30e includes a longitudinal portion 58e with a radiographic marker as shown in FIG. 50. In various embodiments, the guide assembly includes a radio opaque ink for imaging the guide assembly on the model. After imaging, the radiographic markers are identified by the computer software thereby increasing the accuracy of positioning of the objects in virtual space. Existing inks may be employed to prepare the assembly.

Figure 53:
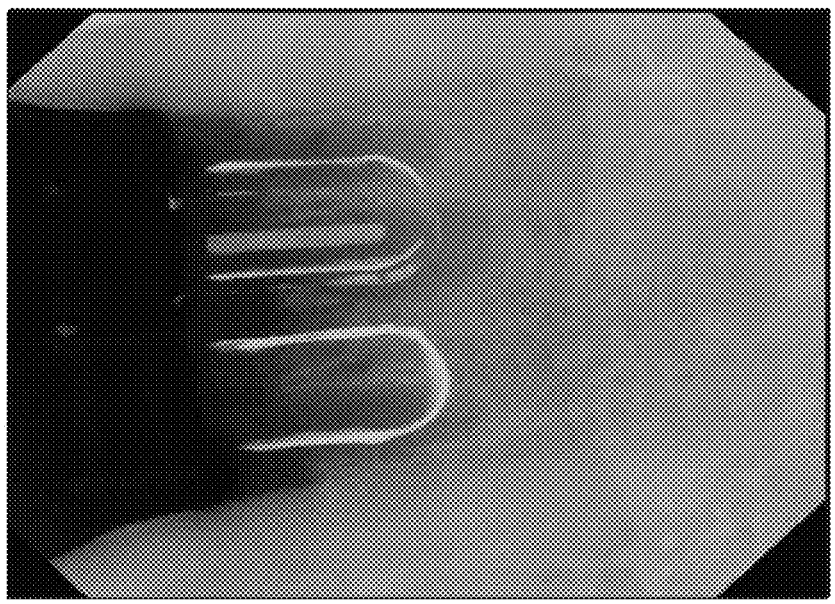
FIGS. 52-53 are an X-ray of the guide system of FIG. 50.
Figure 52:
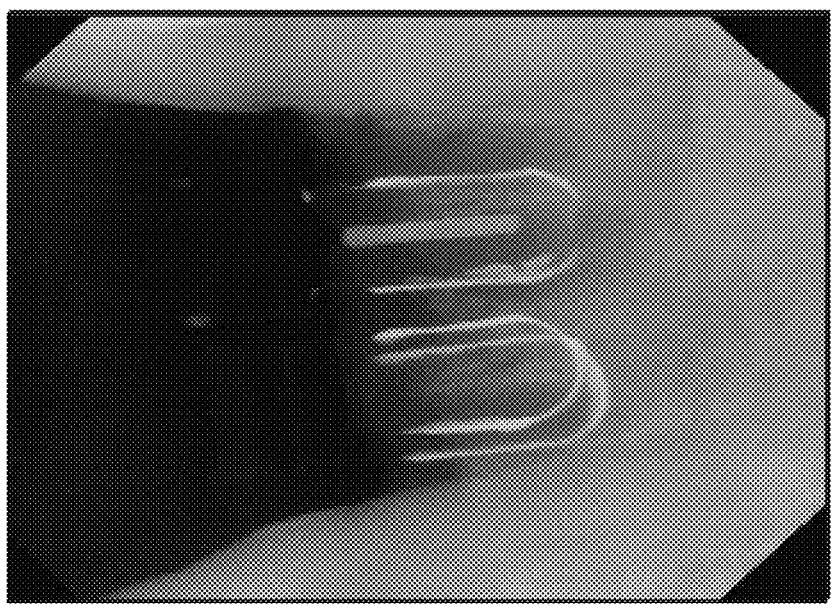

Referring to FIGS. 52-53, the radiographic marker allows a user to quickly and accurately confirm that the X-ray is aligned or not. As shown in FIG. 52, the downward portion of the mounting frame in the foreground and portion in the background are both visible when the X-ray and guide assembly 30e are not aligned. By contrast, in FIG. 53, it is visually apparent from the bright U-shaped image that the downward portions are aligned.

In this manner, the problems inherent in visualizing a 3D object in two dimensions can be overcome. If a user is assured of alignment of the X-ray, the user can consequently be assured of the resulting image accuracy. With existing methods, a user may not know for sure whether the image is aligned. If the X-ray is at an angle, for example, one will appreciate that the resulting image will be distorted. With the method of the present invention, a user is assured of alignment. The user thus can take measurements and verify positioning directly from the resulting image. In the exemplary case, the user inspects the image to ensure that the downward trajectory through the guide inserts are aligned as desired. Readjustments can then be made, if necessary.

Figure 54:
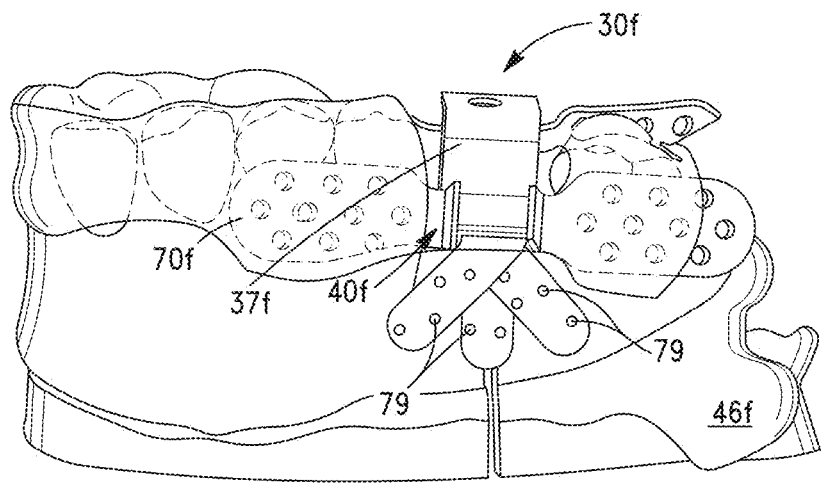
FIG. 54 is a front view of a guide system similar to that of FIG. 33, illustrating the guide system with a radiographic marker in accordance with the present invention.

Turning to FIG. 54, another guide assembly 30f is shown. Guide assembly 30f is similar in many respects to guide assembly 30e but includes downwardly-extending sections 58f having markers 79 attached thereto. The exemplary markers are radiographic markers. Suitable materials include, but are not limited to, metals. Similar to rotation block 37 above, exemplary rotation block 37f is removable. Thus, it may be desirable to accurately locate the rotation block in virtual space after attachment to the mounting frame. To that end, the markers are formed of a material that can be recognized by the computer.

In practice, guide assembly 30f is positioned and adjusted on a model 46f in a manner similar to the methods described above. After the initial positioning, the assembly is imaged on a computer. Exemplary markers 79 are intended for identification on a computer-based system. Given that the positional relationship between the markers and the mounting assembly frame is known, the computer can determine with accuracy the position of the mounting frame based on the markers.

Figure 55:
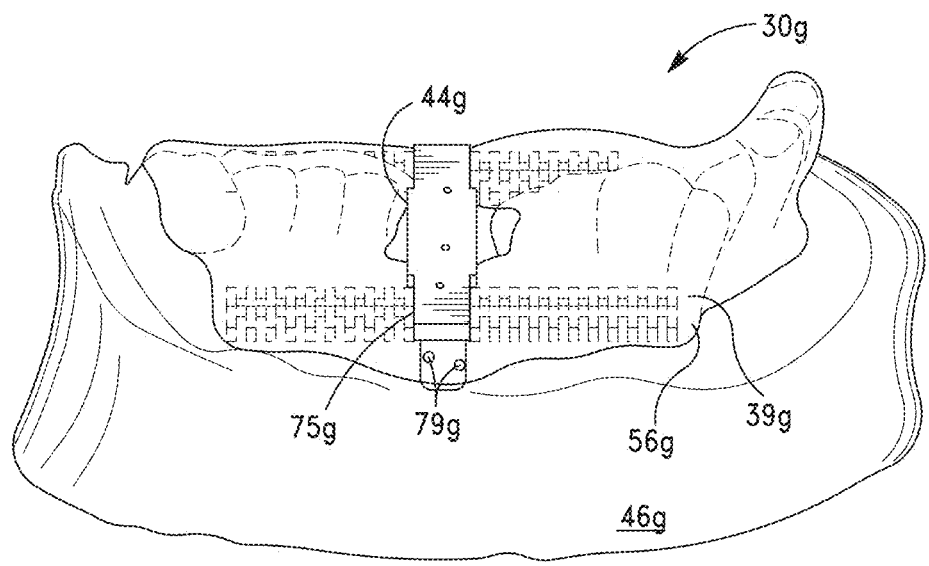
FIG. 55 is a front view of a guide system similar to that of FIG. 47, illustrating a radiographic marker in accordance with the present invention.

FIG. 55 illustrates yet another guide assembly 30g similar to guide assembly 30d except that guide assembly 30g includes radiographic markers 79g. The markers are used similar to the markers 79f described above. Exemplary guide assembly 30f includes a guide insert 75g which embodies the final positioning information from the computer. Similar to guide assembly 30, a guide bore 44g is made in the guide insert based on the final positioning information. The methods for designing and fabricating guide assembly 30g is otherwise similar to the methods described above.

Figure 56:
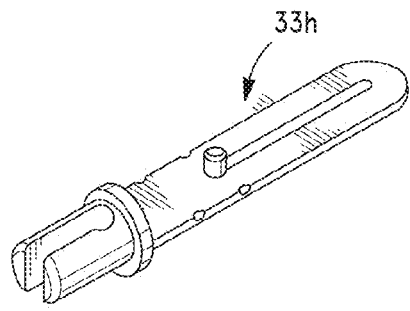
FIG. 56 is a perspective view of a positioning device similar to that shown in FIG. 32.
Figure 57:
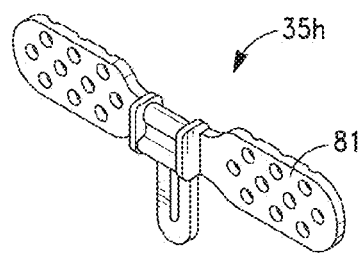
FIGS. 57 and 58 is a perspective views of a flat wing and an L-wing, respectively, of a mounting assembly similar to that shown in FIG. 32.
Figure 58:
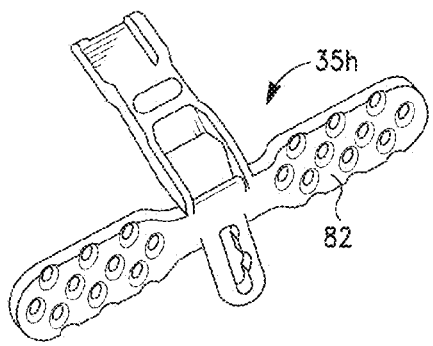

Turning now to FIGS. 56-58, another guide assembly 30h is similar to guide assembly 30d described above except that the mounting assembly is provided with discrete a flat wing 81 and L-wing 82. In various embodiments, the mounting assembly may have a two-piece configuration in which the flat wing may be affixed to the L-wing by a snap connection or other suitable means. Such configuration may facilitate placement of the mounting assembly within a patient's mouth as it allows placement of one wing at a time. One wing may be positioned on the lingual side of the site, and the other wing snapped in place to complete the structure of the mounting assembly. One will appreciate that the mounting assembly may also be provided with two flat wings which may be configured to snap into an appropriately configured receiving block.

Figure 59:
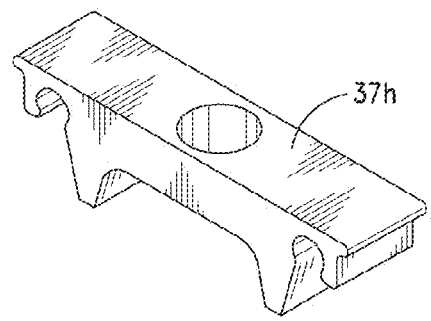
FIGS. 59-67 are perspective views of various rotation blocks similar to that shown in FIG. 32.
Figure 60:
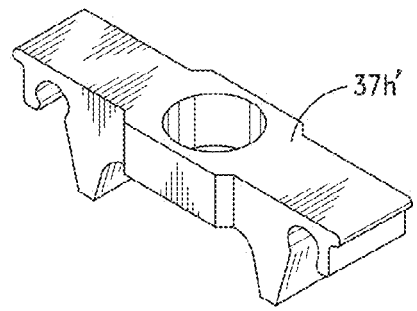
Figure 61:
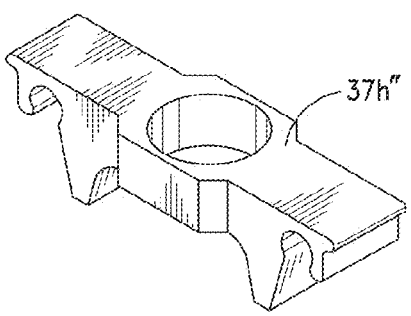
Figure 62:
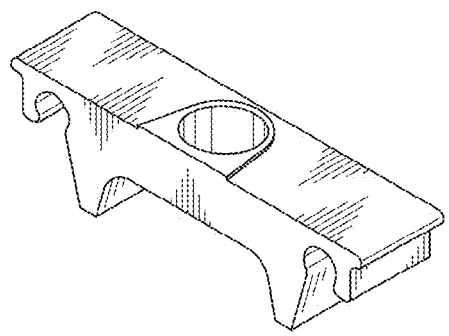
Figure 65:
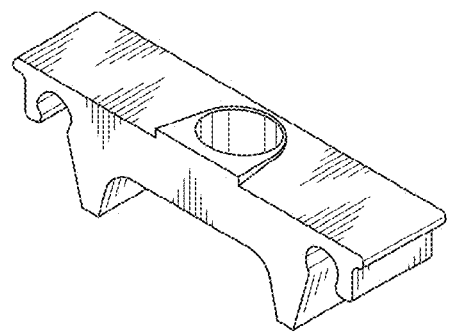
Figure 63:
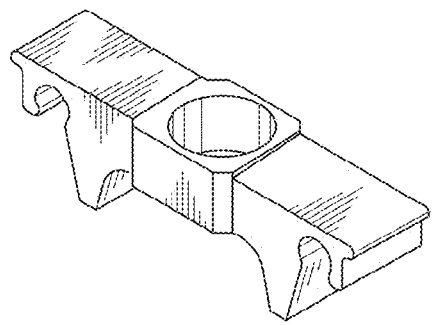
Figure 66:
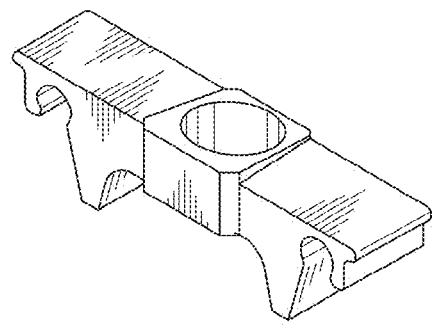
Figure 64:
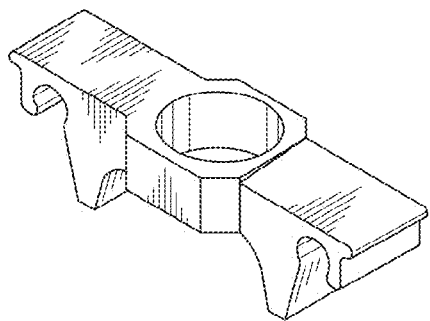
Figure 67:
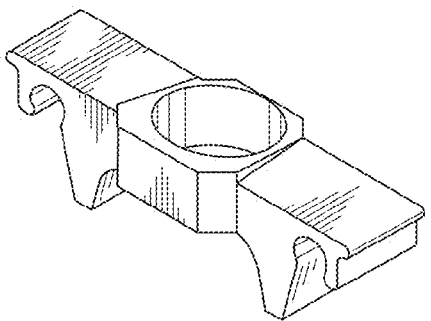

Another feature of guide assembly 30*h* is the provision of rotation blocks sets that include rotation blocks having an assortment of bore diameters. For example, FIGS. 59-61 show a set of 0° rotation blocks 37*h*, 37*h*', 37*h*" having relatively small, medium and large diameter bores, respectively. FIGS. 62-64 show a similar set of 3° rotation blocks, and FIGS. 65-67 show a similar set of 7° rotation blocks. One will appreciate that various diameters may be utilized in accordance with the present invention in order to accommodate various drill and guide diameters. Otherwise, the illustrated rotation blocks may be used in the same manner as those described above.

The methods and surgical guides of the present inventions have several advantages over conventional techniques and guides. The surgical guide of the present invention is fabricated directly from the model accurately and simply with minimal tools. In part because each alignment direction is set in individual steps, the above alignment method provides greater control and repeatability over conventional methods. Further, the same guide assembly (e.g. template and rotation block or guide insert) is aligned on the model and in the mouth thereby eliminating the need for mapping or transferring positional data. The positional data is initially set on the cast model and directly transferred. The method of the present invention may further provide for the alignment to be refined at each step in the process.

The above guide assemblies and methods allow far more accurate translation of positioning information from a model to an implant site for treatment. The final alignment of the surgical guide is the exact position desired. The implant and abutment can be placed confidently with decreased patient visits. Complex instruments are further eliminated. Because of the accurate planning, all implants and components can be preordered, eliminating the need for inventory.

For convenience in explanation and accurate definition in the appended claims, the terms "up" or "upper", "down" or "lower", "inside" and "outside" are used to describe features of the present invention with reference to the positions of such features as displayed in the figures.

In many respects the modifications of the various figures resemble those of preceding modifications and the same reference numerals followed by subscripts "a" and "b" designate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method of preparing a surgical guide for buccal-lingual (BL) and mesial-distal (MD) positioning of a dental implementation, the method comprising:
   preparing a Computer-Aided-Design (CAD) model of a patient's dental arch using a computer system, the CAD model of the patient's dental arch including at least a portion of a jawbone adjacent an edentulous area;
   virtually positioning a positioning device relative to the jawbone adjacent the edentulous area, using the computer system, such that the positioning device is aligned along a BL position axis extending through the jawbone within the edentulous area;
   mapping a virtual template on the CAD model of the patient's dental arch, using the computer system to establish model data;
   manufacturing a physical template and a physical guide insert based on the model data, wherein the physical template removably receives and registers the position of the physical guide insert with respect to the patient's dental arch, and wherein the physical guide insert includes a guide hole extending along the BL position axis.

2. The method of claim 1, wherein the physical guide insert is configured to be positioned above the edentulous area of the patient's dental arch.

3. The method of claim 1, wherein the physical guide insert is configured to be adjustable in a MD direction with respect to the physical template.

4. The method of claim 1, wherein the virtually positioning the positioning device includes translating the positioning device in a BL direction to a desired BL position axis that is in-line with the jawbone region, adjusting a BL angle of the positioning device about a BL pivot axis corresponding to a desired position of a top of the dental implementation to be positioned, the BL pivot axis being located on the BL position axis, and fixing the BL position and the BL angle of the positioning device relative to the model.

5. The method of claim 1, wherein the virtually positioning the positioning device includes setting a z-height of the positioning device.

6. The method of claim 1, further comprising mounting the physical guide insert on the physical template, wherein the mounting includes:
   translating the guide insert in a MD direction to a desired MD position relative to the jawbone region;
   adjusting a preliminary MD angle of the guide insert about an MD pivot axis, the MD pivot axis being coextensive with the BL position axis, and
   affixing the guide insert to the physical template corresponding to the model.

7. The method of claim 1, further comprising mounting the physical guide insert on the physical template, wherein the mounting includes:
   translating the guide insert in a MD direction to a desired MD position relative to the jawbone region.

8. The method of claim 1, further comprising mounting the physical guide insert on the physical template, wherein the mounting includes:
   adjusting a preliminary MD angle of the guide insert about an MD pivot axis, the MD pivot axis being coextensive with the BL position axis.

9. A system for preparing a surgical guide for buccal-lingual (BL) and mesial-distal (MD) positioning of a dental implementation, the system comprising:
   a computer system configured to prepare a Computer-Aided-Design (CAD) model of a patient's dental arch, the CAD model of the patient's dental arch including at least a portion of a jawbone adjacent an edentulous area;
   the computer system being configured to virtually position a positioning device relative to the jawbone adjacent the edentulous area, such that the positioning device is aligned along a BL position axis extending through the jawbone within the edentulous area;
   the computer system being configured to map a virtual template on the CAD model of the patient's dental arch, using the computer system to establish model data;

one or more manufacturing devices configured to manufacture a physical template and a physical guide insert based on the model data, wherein the physical template removably receives and registers the position of the physical guide insert with respect to the patient's dental arch, and wherein the physical guide assembly includes a guide hole extending along the BL position axis.

10. The system of claim 9, wherein the physical guide insert is configured to be positioned above the edentulous area of the patient's dental arch.

11. The system of claim 9, wherein the physical guide insert is configured to be adjustable in a MD direction with respect to the physical template.

12. The system of claim 9, wherein computer system is configured to virtually position the positioning device by translating the positioning device in a BL direction to a desired BL position axis that is in-line with the jawbone region, adjusting a BL angle of the positioning device about a BL pivot axis corresponding to a desired position of a top of the dental implementation to be positioned, the BL pivot axis being located on the BL position axis, and fixing the BL position and the BL angle of the positioning device relative to the model.

13. The system of claim 9, wherein the computer system is configured to virtually position the positioning device at a z-height of the positioning device.

* * * * *